US011951263B2

(12) United States Patent
Khuu et al.

(10) Patent No.: US 11,951,263 B2
(45) Date of Patent: Apr. 9, 2024

(54) MULTI-DIRECTION STEERABLE HANDLES

(71) Applicant: Edwards Lifesciences Corporation, Irvine, CA (US)

(72) Inventors: Bao Khuu, Irvine, CA (US); Matthew T. Winston, Aliso Viejo, CA (US); Asher L. Metchik, Rolling Hills Estates, CA (US); Eric Robert Dixon, Villa Park, CA (US)

(73) Assignee: EDWARDS LIFESCIENCES CORPORATION, Irvine, CA (US)

(*) Notice: Subject to any disclaimer, the term of this patent is extended or adjusted under 35 U.S.C. 154(b) by 750 days.

(21) Appl. No.: 17/066,395

(22) Filed: Oct. 8, 2020

(65) Prior Publication Data
US 2021/0023338 A1 Jan. 28, 2021

Related U.S. Application Data

(63) Continuation of application No. 15/453,735, filed on Mar. 8, 2017, now Pat. No. 10,799,675.

(60) Provisional application No. 62/311,031, filed on Mar. 21, 2016.

(51) Int. Cl.
A61M 25/01 (2006.01)
A61F 2/24 (2006.01)
A61F 2/95 (2013.01)

(52) U.S. Cl.
CPC ....... A61M 25/0136 (2013.01); A61F 2/2427 (2013.01); A61M 25/0147 (2013.01); A61F 2/9517 (2020.05)

(58) Field of Classification Search
CPC ........... A61M 25/0136; A61M 25/0147; A61F 2/2427; A61F 2/9517; A61F 2/95
See application file for complete search history.

(56) References Cited

U.S. PATENT DOCUMENTS 3,874,388 A 4/1975 King et al.
4,340,091 A 7/1982 Skelton et al.
(Continued)

FOREIGN PATENT DOCUMENTS

CN 1142351 A 2/1997
CN 106175845 A 12/2016
(Continued)

OTHER PUBLICATIONS

Grasso et al., "The PASCAL transcatheter mitral valve repair system for the treatment of mitral regurgitation: another piece to the puzzle of edge-to-edge technique", Journal of Thoracic Disease, vol. 9, No. 12, pp. 4856-4859, Dec. 2017, doi:10.21037/jtd.2017.10.156, AME Publishing Company, Hong Kong, China.
(Continued)

Primary Examiner — Ariana Zimbouski
Assistant Examiner — John A Doubrava
(74) Attorney, Agent, or Firm — Anya Adams

(57) ABSTRACT

Disclosed herein are catheter control handles that include various mechanisms for controlling the circumferential angle and radial magnitude of flexion of an attached catheter. Control handles can comprise a housing. Control wires extend from a distal end of the housing and into a steerable transluminal device. A flex control member is operable to control tension on the pull wires to adjust a magnitude of radial flexion of the steerable transluminal device. A position control member is operable to control tension on the pull wires to adjust a circumferential angle in which the radial flexion of the steerable transluminal device is directed.

13 Claims, 10 Drawing Sheets

(56) References Cited

U.S. PATENT DOCUMENTS

| | | |
|---|---|---|
| 4,506,669 A | 3/1985 | Blake, III |
| 4,590,937 A | 5/1986 | Deniega |
| 4,693,248 A | 9/1987 | Failla |
| 4,803,983 A | 2/1989 | Siegel |
| 5,125,895 A | 6/1992 | Buchbinder et al. |
| 5,171,252 A | 12/1992 | Friedland |
| 5,195,962 A | 3/1993 | Martin et al. |
| 5,292,326 A | 3/1994 | Green et al. |
| 5,327,905 A | 7/1994 | Avitall |
| 5,363,861 A | 11/1994 | Edwards et al. |
| 5,370,685 A | 12/1994 | Stevens |
| 5,389,077 A | 2/1995 | Melinyshyn et al. |
| 5,411,552 A | 5/1995 | Andersen et al. |
| 5,450,860 A | 9/1995 | O'Connor |
| 5,456,674 A | 10/1995 | Bos et al. |
| 5,474,057 A | 12/1995 | Makower et al. |
| 5,478,353 A | 12/1995 | Yoon |
| 5,487,746 A | 1/1996 | Yu et al. |
| 5,565,004 A | 10/1996 | Christoudias |
| 5,607,462 A | 3/1997 | Imran |
| 5,609,598 A | 3/1997 | Laufer et al. |
| 5,611,794 A | 3/1997 | Sauer et al. |
| 5,626,607 A | 5/1997 | Malecki et al. |
| 5,695,504 A | 12/1997 | Gifford, III et al. |
| 5,716,417 A | 2/1998 | Girard et al. |
| 5,727,569 A | 3/1998 | Benetti et al. |
| 5,741,297 A | 4/1998 | Simon |
| 5,782,746 A | 7/1998 | Wright |
| 5,797,960 A | 8/1998 | Stevens et al. |
| 5,836,311 A | 11/1998 | Borst et al. |
| 5,843,076 A | 12/1998 | Webster, Jr. et al. |
| 5,855,590 A | 1/1999 | Malecki et al. |
| 5,885,271 A | 3/1999 | Hamilton et al. |
| 5,888,247 A | 3/1999 | Benetti |
| 5,891,017 A | 4/1999 | Swindle et al. |
| 5,891,088 A | 4/1999 | Thompson et al. |
| 5,891,112 A | 4/1999 | Samson |
| 5,894,843 A | 4/1999 | Benetti et al. |
| 5,921,979 A | 7/1999 | Kovac et al. |
| 5,944,738 A | 8/1999 | Amplatz et al. |
| 5,957,835 A | 9/1999 | Anderson et al. |
| 5,972,020 A | 10/1999 | Carpentier et al. |
| 5,980,534 A | 11/1999 | Gimpelson |
| 6,004,329 A | 12/1999 | Myers et al. |
| 6,010,531 A | 1/2000 | Donlon et al. |
| 6,017,358 A | 1/2000 | Yoon et al. |
| 6,086,600 A | 7/2000 | Kortenbach |
| 6,120,496 A | 9/2000 | Whayne et al. |
| 6,132,370 A | 10/2000 | Furnish et al. |
| 6,162,239 A | 12/2000 | Manhes |
| 6,165,183 A | 12/2000 | Kuehn et al. |
| 6,182,664 B1 | 2/2001 | Cosgrove |
| 6,193,732 B1 | 2/2001 | Frantzen et al. |
| 6,193,734 B1 | 2/2001 | Bolduc et al. |
| 6,200,315 B1 | 3/2001 | Gaiser et al. |
| 6,228,032 B1 | 5/2001 | Eaton et al. |
| 6,241,743 B1 | 6/2001 | Levin et al. |
| 6,269,819 B1 | 8/2001 | Oz et al. |
| 6,269,829 B1 | 8/2001 | Chen et al. |
| 6,312,447 B1 | 11/2001 | Grimes |
| 6,461,366 B1 | 10/2002 | Seguin |
| 6,468,285 B1 | 10/2002 | Hsu et al. |
| 6,508,806 B1 | 1/2003 | Hoste |
| 6,508,825 B1 | 1/2003 | Selmon et al. |
| 6,530,933 B1 | 3/2003 | Yeung et al. |
| 6,537,290 B2 | 3/2003 | Adams et al. |
| 6,544,215 B1 | 4/2003 | Bencini et al. |
| 6,626,930 B1 | 9/2003 | Allen et al. |
| 6,629,534 B1 | 10/2003 | Goar et al. |
| 6,719,767 B1 | 4/2004 | Kimblad |
| 6,764,510 B2 | 7/2004 | Vidlund et al. |
| 6,770,083 B2 | 8/2004 | Seguin |
| 6,837,867 B2 | 1/2005 | Kortelling |
| 6,855,137 B2 | 2/2005 | Bon |
| 6,913,614 B2 | 7/2005 | Marino et al. |
| 6,939,337 B2 | 9/2005 | Parker et al. |
| 6,945,956 B2 | 9/2005 | Waldhauser et al. |
| 7,048,754 B2 | 5/2006 | Martin et al. |
| 7,101,395 B2 | 9/2006 | Tremulis et al. |
| 7,125,421 B2 | 10/2006 | Tremulis et al. |
| 7,288,097 B2 | 10/2007 | Seguin |
| 7,371,210 B2 | 5/2008 | Brock et al. |
| 7,464,712 B2 | 12/2008 | Oz et al. |
| 7,509,959 B2 | 3/2009 | Oz et al. |
| 7,569,062 B1 | 8/2009 | Kuehn et al. |
| 7,618,449 B2 | 11/2009 | Tremulis et al. |
| 7,682,369 B2 | 3/2010 | Seguin |
| 7,731,706 B2 | 6/2010 | Potter |
| 7,744,609 B2 | 6/2010 | Allen et al. |
| 7,748,389 B2 | 7/2010 | Salahieh et al. |
| 7,753,932 B2 | 7/2010 | Gingrich et al. |
| 7,758,596 B2 | 7/2010 | Oz et al. |
| 7,780,723 B2 | 8/2010 | Taylor |
| 7,803,185 B2 | 9/2010 | Gabbay |
| 7,824,443 B2 | 11/2010 | Salahieh et al. |
| 7,981,123 B2 | 7/2011 | Seguin |
| 7,988,724 B2 | 8/2011 | Salahieh et al. |
| 8,052,750 B2 | 11/2011 | Tuval et al. |
| 8,070,805 B2 | 12/2011 | Vidlund et al. |
| 8,096,985 B2 | 1/2012 | Legaspi et al. |
| 8,104,149 B1 | 1/2012 | McGarity |
| 8,133,239 B2 | 3/2012 | Oz et al. |
| 8,147,542 B2 | 4/2012 | Maisano et al. |
| 8,172,856 B2 | 5/2012 | Eigler et al. |
| 8,206,437 B2 | 6/2012 | Bonhoeffer et al. |
| 8,216,301 B2 | 7/2012 | Bonhoeffer et al. |
| 8,303,653 B2 | 11/2012 | Bonhoeffer et al. |
| 8,313,525 B2 | 11/2012 | Tuval et al. |
| 8,348,995 B2 | 1/2013 | Tuval et al. |
| 8,348,996 B2 | 1/2013 | Tuval et al. |
| 8,414,643 B2 | 4/2013 | Tuval et al. |
| 8,425,404 B2 | 4/2013 | Wilson et al. |
| 8,449,599 B2 | 5/2013 | Chau et al. |
| 8,449,606 B2 | 5/2013 | Eliasen et al. |
| 8,460,368 B2 | 6/2013 | Taylor et al. |
| 8,470,028 B2 | 6/2013 | Thornton et al. |
| 8,480,730 B2 | 7/2013 | Maurer et al. |
| 8,540,767 B2 | 9/2013 | Zhang |
| 8,579,965 B2 | 11/2013 | Bonhoeffer et al. |
| 8,585,756 B2 | 11/2013 | Bonhoeffer et al. |
| 8,652,202 B2 | 2/2014 | Alon et al. |
| 8,668,733 B2 | 3/2014 | Haug et al. |
| 8,721,665 B2 | 5/2014 | Oz et al. |
| 8,740,918 B2 | 6/2014 | Seguin |
| 8,771,347 B2 | 7/2014 | DeBoer et al. |
| 8,778,017 B2 | 7/2014 | Eliasen et al. |
| 8,834,564 B2 | 9/2014 | Tuval et al. |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,945,177 B2 | 2/2015 | Dell et al. |
| 9,034,032 B2 | 5/2015 | McLean et al. |
| 9,198,757 B2 | 12/2015 | Schroeder et al. |
| 9,220,507 B1 | 12/2015 | Patel et al. |
| 9,259,317 B2 | 2/2016 | Wilson et al. |
| 9,282,972 B1 | 3/2016 | Patel et al. |
| 9,301,834 B2 | 4/2016 | Tuval et al. |
| 9,308,360 B2 | 4/2016 | Bishop et al. |
| 9,387,071 B2 | 7/2016 | Tuval et al. |
| 9,427,327 B2 | 8/2016 | Parrish |
| 9,439,763 B2 | 9/2016 | Geist et al. |
| 9,510,837 B2 | 12/2016 | Seguin |
| 9,510,946 B2 | 12/2016 | Chau et al. |
| 9,572,660 B2 | 2/2017 | Braido et al. |
| 9,642,704 B2 | 5/2017 | Tuval et al. |
| 9,700,445 B2 | 7/2017 | Martin et al. |
| 9,775,963 B2 | 10/2017 | Miller |
| D809,139 S | 1/2018 | Marsot et al. |
| 9,889,002 B2 | 2/2018 | Bonhoeffer et al. |
| 9,949,824 B2 | 4/2018 | Bonhoeffer et al. |
| 10,076,327 B2 | 9/2018 | Ellis et al. |
| 10,076,415 B1 | 9/2018 | Metchik et al. |
| 10,099,050 B2 | 10/2018 | Chen et al. |
| 10,105,221 B2 | 10/2018 | Siegel |

(56) References Cited

U.S. PATENT DOCUMENTS

| | | |
|---|---|---|
| 10,105,222 B1 | 10/2018 | Metchik et al. |
| 10,111,751 B1 | 10/2018 | Metchik et al. |
| 10,123,873 B1 | 11/2018 | Metchik et al. |
| 10,130,475 B1 | 11/2018 | Metchik et al. |
| 10,136,993 B1 | 11/2018 | Metchik et al. |
| 10,159,570 B1 | 12/2018 | Metchik et al. |
| 10,226,309 B2 | 3/2019 | Ho et al. |
| 10,231,837 B1 | 3/2019 | Metchik et al. |
| 10,238,493 B1 | 3/2019 | Metchik et al. |
| 10,238,494 B2 | 3/2019 | McNiven et al. |
| 10,238,495 B2 | 3/2019 | Marsot et al. |
| 10,299,924 B2 | 5/2019 | Kizuka |
| 10,376,673 B2 | 8/2019 | Van Hoven et al. |
| 10,537,348 B2 | 1/2020 | Rodriguez-Navarro et al. |
| 10,575,841 B1 | 3/2020 | Paulos |
| 11,219,746 B2 * | 1/2022 | Khuu ................. A61F 2/2427 |
| 2001/0005787 A1 | 6/2001 | Oz et al. |
| 2002/0013571 A1 | 1/2002 | Goldfarb et al. |
| 2002/0107531 A1 | 8/2002 | Schreck et al. |
| 2002/0173811 A1 | 11/2002 | Tu et al. |
| 2002/0183787 A1 | 12/2002 | Wahr et al. |
| 2003/0144573 A1 | 7/2003 | Heilman et al. |
| 2003/0187467 A1 | 10/2003 | Schreck |
| 2003/0208231 A1 | 11/2003 | Williamson et al. |
| 2004/0003819 A1 | 1/2004 | St. Goar et al. |
| 2004/0030382 A1 | 2/2004 | St. Goar et al. |
| 2004/0034365 A1 | 2/2004 | Lentz et al. |
| 2004/0044350 A1 | 3/2004 | Martin et al. |
| 2004/0044365 A1 | 3/2004 | Bachman |
| 2004/0049207 A1 | 3/2004 | Goldfarb et al. |
| 2004/0122448 A1 | 6/2004 | Levine |
| 2004/0127981 A1 | 7/2004 | Rahdert et al. |
| 2004/0127982 A1 | 7/2004 | Machold et al. |
| 2004/0147943 A1 | 7/2004 | Kobayashi |
| 2004/0181135 A1 | 9/2004 | Drysen |
| 2004/0181206 A1 | 9/2004 | Chiu et al. |
| 2004/0181238 A1 | 9/2004 | Zarbatany et al. |
| 2004/0210307 A1 | 10/2004 | Khairkhahan |
| 2004/0220593 A1 | 11/2004 | Greenhalgh |
| 2005/0010287 A1 | 1/2005 | Macoviak et al. |
| 2005/0049618 A1 | 3/2005 | Masuda et al. |
| 2005/0070926 A1 | 3/2005 | Ortiz |
| 2005/0137690 A1 | 6/2005 | Salahieh et al. |
| 2005/0143767 A1 | 6/2005 | Kimura et al. |
| 2005/0165429 A1 | 7/2005 | Douglas et al. |
| 2005/0216039 A1 | 9/2005 | Lederman |
| 2005/0251183 A1 | 11/2005 | Buckman et al. |
| 2005/0288786 A1 | 12/2005 | Chanduszko |
| 2006/0020275 A1 | 1/2006 | Goldfarb et al. |
| 2006/0089671 A1 | 4/2006 | Goldfarb et al. |
| 2006/0100649 A1 | 5/2006 | Hart |
| 2006/0122647 A1 | 6/2006 | Callaghan et al. |
| 2006/0142694 A1 | 6/2006 | Bednarek et al. |
| 2006/0173251 A1 | 8/2006 | Govari et al. |
| 2006/0178700 A1 | 8/2006 | Quinn |
| 2006/0224169 A1 | 10/2006 | Weisenburgh et al. |
| 2007/0010800 A1 | 1/2007 | Weitzner et al. |
| 2007/0010877 A1 | 1/2007 | Salahieh et al. |
| 2007/0016286 A1 | 1/2007 | Herrmann et al. |
| 2007/0021779 A1 | 1/2007 | Garvin et al. |
| 2007/0032807 A1 | 2/2007 | Ortiz et al. |
| 2007/0093857 A1 | 4/2007 | Rogers et al. |
| 2007/0093890 A1 | 4/2007 | Eliasen et al. |
| 2007/0156197 A1 | 7/2007 | Root et al. |
| 2007/0191154 A1 | 8/2007 | Genereux et al. |
| 2007/0197858 A1 | 8/2007 | Goldfarb et al. |
| 2007/0198038 A1 | 8/2007 | Cohen et al. |
| 2007/0265700 A1 | 11/2007 | Eliasen et al. |
| 2007/0282414 A1 | 12/2007 | Soltis et al. |
| 2007/0293943 A1 | 12/2007 | Quinn |
| 2007/0299387 A1 | 12/2007 | Williams et al. |
| 2007/0299424 A1 | 12/2007 | Cumming et al. |
| 2008/0039743 A1 | 2/2008 | Fox et al. |
| 2008/0039953 A1 | 2/2008 | Davis et al. |
| 2008/0065149 A1 | 3/2008 | Thielen et al. |
| 2008/0077144 A1 | 3/2008 | Crofford |
| 2008/0091169 A1 | 4/2008 | Heideman et al. |
| 2008/0140089 A1 | 6/2008 | Kogiso et al. |
| 2008/0147093 A1 | 6/2008 | Roskopf et al. |
| 2008/0147112 A1 | 6/2008 | Sheets et al. |
| 2008/0149685 A1 | 6/2008 | Smith et al. |
| 2008/0167713 A1 | 7/2008 | Bolling |
| 2008/0177300 A1 | 7/2008 | Mas et al. |
| 2008/0208332 A1 | 8/2008 | Lamphere et al. |
| 2008/0221672 A1 | 9/2008 | Lamphere et al. |
| 2008/0255427 A1 | 10/2008 | Satake et al. |
| 2008/0281411 A1 | 11/2008 | Berreklouw |
| 2008/0287862 A1 | 11/2008 | Weitzner et al. |
| 2008/0294247 A1 | 11/2008 | Yang et al. |
| 2008/0312506 A1 * | 12/2008 | Spivey .............. A61M 25/0138 600/149 |
| 2008/0319455 A1 | 12/2008 | Harris et al. |
| 2009/0005863 A1 | 1/2009 | Goetz et al. |
| 2009/0024110 A1 | 1/2009 | Heideman et al. |
| 2009/0131880 A1 | 5/2009 | Speziali et al. |
| 2009/0156995 A1 | 6/2009 | Martin et al. |
| 2009/0163934 A1 | 6/2009 | Raschdorf, Jr. et al. |
| 2009/0166913 A1 | 7/2009 | Guo et al. |
| 2009/0177266 A1 | 7/2009 | Powell et al. |
| 2009/0234280 A1 | 9/2009 | Tah et al. |
| 2009/0275902 A1 | 11/2009 | Heeps et al. |
| 2009/0287304 A1 | 11/2009 | Dahlgren et al. |
| 2010/0022823 A1 | 1/2010 | Goldfarb et al. |
| 2010/0057192 A1 | 3/2010 | Celermajer |
| 2010/0069834 A1 | 3/2010 | Schultz |
| 2010/0094317 A1 | 4/2010 | Goldfarb et al. |
| 2010/0106141 A1 | 4/2010 | Osypka et al. |
| 2010/0121434 A1 | 5/2010 | Paul et al. |
| 2010/0249497 A1 | 9/2010 | Peine et al. |
| 2010/0298929 A1 | 11/2010 | Thornton et al. |
| 2010/0324595 A1 | 12/2010 | Linder et al. |
| 2011/0082538 A1 | 4/2011 | Dahlgren et al. |
| 2011/0137410 A1 | 6/2011 | Hacohen |
| 2011/0168180 A1 | 7/2011 | Lugtigheid |
| 2011/0245855 A1 | 10/2011 | Matsuoka et al. |
| 2011/0257723 A1 | 10/2011 | McNamara |
| 2011/0295281 A1 | 12/2011 | Mizumoto et al. |
| 2012/0022633 A1 | 1/2012 | Olson et al. |
| 2012/0089125 A1 | 4/2012 | Scheibe et al. |
| 2012/0109160 A1 | 5/2012 | Martinez et al. |
| 2012/0116419 A1 | 5/2012 | Sigmon, Jr. |
| 2012/0209318 A1 | 8/2012 | Qadeer |
| 2012/0277853 A1 | 11/2012 | Rothstein |
| 2013/0035759 A1 | 2/2013 | Gross et al. |
| 2013/0041314 A1 | 2/2013 | Dillon |
| 2013/0066341 A1 | 3/2013 | Ketai et al. |
| 2013/0066342 A1 | 3/2013 | Dell et al. |
| 2013/0072945 A1 | 3/2013 | Terada |
| 2013/0073034 A1 | 3/2013 | Wilson et al. |
| 2013/0110254 A1 | 5/2013 | Osborne |
| 2013/0190798 A1 | 7/2013 | Kapadia |
| 2013/0190861 A1 | 7/2013 | Chau et al. |
| 2013/0268069 A1 | 10/2013 | Zakai et al. |
| 2013/0282059 A1 | 10/2013 | Ketai et al. |
| 2013/0304197 A1 | 11/2013 | Buchbinder et al. |
| 2013/0325110 A1 | 12/2013 | Khalil et al. |
| 2014/0031928 A1 | 1/2014 | Murphy et al. |
| 2014/0046433 A1 | 2/2014 | Kovalsky |
| 2014/0046434 A1 | 2/2014 | Rolando et al. |
| 2014/0052237 A1 | 2/2014 | Lane et al. |
| 2014/0058411 A1 | 2/2014 | Soutorine et al. |
| 2014/0067048 A1 | 3/2014 | Chau et al. |
| 2014/0067052 A1 | 3/2014 | Chau et al. |
| 2014/0094903 A1 | 4/2014 | Miller et al. |
| 2014/0135685 A1 | 5/2014 | Kabe et al. |
| 2014/0194975 A1 | 7/2014 | Quill et al. |
| 2014/0200662 A1 | 7/2014 | Eftel et al. |
| 2014/0207231 A1 | 7/2014 | Hacohen et al. |
| 2014/0236198 A1 | 8/2014 | Goldfarb et al. |
| 2014/0243968 A1 | 8/2014 | Padala |
| 2014/0251042 A1 | 9/2014 | Asselin et al. |
| 2014/0277404 A1 | 9/2014 | Wilson et al. |
| 2014/0277411 A1 | 9/2014 | Bortlein et al. |
| 2014/0277427 A1 | 9/2014 | Ratz et al. |

(56) References Cited

U.S. PATENT DOCUMENTS

| | | |
|---|---|---|
| 2014/0316428 A1 | 10/2014 | Golan |
| 2014/0324164 A1 | 10/2014 | Gross et al. |
| 2014/0330368 A1 | 11/2014 | Gloss et al. |
| 2014/0336751 A1 | 11/2014 | Kramer |
| 2014/0371843 A1 | 12/2014 | Wilson et al. |
| 2015/0039084 A1 | 2/2015 | Levi et al. |
| 2015/0057704 A1 | 2/2015 | Takahashi |
| 2015/0094802 A1 | 4/2015 | Buchbinder et al. |
| 2015/0100116 A1 | 4/2015 | Mohl et al. |
| 2015/0105808 A1 | 4/2015 | Gordon et al. |
| 2015/0148896 A1 | 5/2015 | Karapetian et al. |
| 2015/0157268 A1 | 6/2015 | Winshtein et al. |
| 2015/0196390 A1 | 7/2015 | Ma et al. |
| 2015/0223793 A1 | 8/2015 | Goldfarb et al. |
| 2015/0230919 A1 | 8/2015 | Chau et al. |
| 2015/0238313 A1 | 8/2015 | Spence et al. |
| 2015/0257757 A1 | 9/2015 | Powers et al. |
| 2015/0257877 A1 | 9/2015 | Hernandez |
| 2015/0257883 A1 | 9/2015 | Basude et al. |
| 2015/0313592 A1 | 11/2015 | Coillard-Lavirotte et al. |
| 2015/0351904 A1 | 12/2015 | Cooper et al. |
| 2015/0366666 A1 | 12/2015 | Khairkhahan et al. |
| 2016/0008131 A1 | 1/2016 | Christianson et al. |
| 2016/0022970 A1 | 1/2016 | Forcucci et al. |
| 2016/0051796 A1 | 2/2016 | Kanemasa et al. |
| 2016/0074164 A1 | 3/2016 | Naor |
| 2016/0074165 A1 | 3/2016 | Spence et al. |
| 2016/0106539 A1 | 4/2016 | Buchbinder et al. |
| 2016/0113762 A1 | 4/2016 | Clague et al. |
| 2016/0113764 A1 | 4/2016 | Sheahan et al. |
| 2016/0113766 A1 | 4/2016 | Ganesan et al. |
| 2016/0155987 A1 | 6/2016 | Yoo et al. |
| 2016/0174979 A1 | 6/2016 | Wei |
| 2016/0174981 A1 | 6/2016 | Fago et al. |
| 2016/0242906 A1 | 8/2016 | Morriss et al. |
| 2016/0287387 A1 | 10/2016 | Wei |
| 2016/0317290 A1 | 11/2016 | Chau et al. |
| 2016/0331523 A1 | 11/2016 | Chau et al. |
| 2016/0354082 A1 | 12/2016 | Oz et al. |
| 2017/0020521 A1 | 1/2017 | Krone et al. |
| 2017/0035561 A1 | 2/2017 | Rowe et al. |
| 2017/0035566 A1 | 2/2017 | Krone et al. |
| 2017/0042456 A1 | 2/2017 | Budiman |
| 2017/0042678 A1 | 2/2017 | Ganesan et al. |
| 2017/0049455 A1 | 2/2017 | Seguin |
| 2017/0100119 A1 | 4/2017 | Baird et al. |
| 2017/0100236 A1 | 4/2017 | Robertson et al. |
| 2017/0224955 A1 | 8/2017 | Douglas et al. |
| 2017/0239048 A1 | 8/2017 | Goldfarb et al. |
| 2017/0252154 A1 | 9/2017 | Tubishevitz et al. |
| 2017/0266413 A1 | 9/2017 | Khuu et al. |
| 2017/0281330 A1 | 10/2017 | Liljegren et al. |
| 2017/0348102 A1 | 12/2017 | Cousins et al. |
| 2018/0008311 A1 | 1/2018 | Shiroff et al. |
| 2018/0021044 A1 | 1/2018 | Miller et al. |
| 2018/0021129 A1 | 1/2018 | Peterson et al. |
| 2018/0021134 A1 | 1/2018 | McNiven et al. |
| 2018/0071488 A1 | 3/2018 | Khuu et al. |
| 2018/0071489 A1 | 3/2018 | Khuu et al. |
| 2018/0078271 A1 | 3/2018 | Thrasher, III |
| 2018/0092661 A1 | 4/2018 | Prabhu |
| 2018/0126124 A1 | 5/2018 | Winston et al. |
| 2018/0133008 A1 | 5/2018 | Kizuka et al. |
| 2018/0146964 A1 | 5/2018 | Garcia et al. |
| 2018/0146966 A1 | 5/2018 | Hernandez et al. |
| 2018/0153552 A1 | 6/2018 | King et al. |
| 2018/0161159 A1 | 6/2018 | Lee et al. |
| 2018/0168803 A1 | 6/2018 | Pesce et al. |
| 2018/0185154 A1 | 7/2018 | Cao |
| 2018/0221147 A1 | 8/2018 | Ganesan et al. |
| 2018/0235657 A1 | 8/2018 | Abunassar |
| 2018/0243086 A1 | 8/2018 | Barbarino et al. |
| 2018/0258665 A1 | 9/2018 | Reddy et al. |
| 2018/0263767 A1 | 9/2018 | Chau et al. |
| 2018/0296326 A1 | 10/2018 | Dixon et al. |
| 2018/0296327 A1 | 10/2018 | Dixon et al. |
| 2018/0296328 A1 | 10/2018 | Dixon et al. |
| 2018/0296329 A1 | 10/2018 | Dixon et al. |
| 2018/0296330 A1 | 10/2018 | Dixon et al. |
| 2018/0296331 A1 | 10/2018 | Dixon et al. |
| 2018/0296332 A1 | 10/2018 | Dixon et al. |
| 2018/0296333 A1 | 10/2018 | Dixon et al. |
| 2018/0296334 A1 | 10/2018 | Dixon et al. |
| 2018/0325661 A1 | 11/2018 | Delgado et al. |
| 2018/0325671 A1 | 11/2018 | Abunassar et al. |
| 2018/0333259 A1 | 11/2018 | Dibie |
| 2018/0344457 A1 | 12/2018 | Gross et al. |
| 2018/0353181 A1 | 12/2018 | Wei |
| 2019/0000613 A1 | 1/2019 | Delgado et al. |
| 2019/0000623 A1 | 1/2019 | Pan et al. |
| 2019/0008642 A1 | 1/2019 | Delgado et al. |
| 2019/0008643 A1 | 1/2019 | Delgado et al. |
| 2019/0015199 A1 | 1/2019 | Delgado et al. |
| 2019/0015200 A1 | 1/2019 | Delgado et al. |
| 2019/0015207 A1 | 1/2019 | Delgado et al. |
| 2019/0015208 A1 | 1/2019 | Delgado et al. |
| 2019/0021851 A1 | 1/2019 | Delgado et al. |
| 2019/0021852 A1 | 1/2019 | Delgado et al. |
| 2019/0029498 A1 | 1/2019 | Mankowski et al. |
| 2019/0029810 A1 | 1/2019 | Delgado et al. |
| 2019/0029813 A1 | 1/2019 | Delgado et al. |
| 2019/0030285 A1 | 1/2019 | Prabhu et al. |
| 2019/0053810 A1 | 2/2019 | Griffin |
| 2019/0060058 A1 | 2/2019 | Delgado et al. |
| 2019/0060059 A1 | 2/2019 | Delgado et al. |
| 2019/0060072 A1 | 2/2019 | Zeng |
| 2019/0060073 A1 | 2/2019 | Delgado et al. |
| 2019/0060074 A1 | 2/2019 | Delgado et al. |
| 2019/0060075 A1 | 2/2019 | Delgado et al. |
| 2019/0069991 A1 | 3/2019 | Metchik et al. |
| 2019/0069992 A1 | 3/2019 | Delgado et al. |
| 2019/0069993 A1 | 3/2019 | Delgado et al. |
| 2019/0105156 A1 | 4/2019 | He et al. |
| 2019/0111239 A1 | 4/2019 | Bolduc et al. |
| 2019/0117113 A1 | 4/2019 | Curran |
| 2019/0142589 A1 | 5/2019 | Basude |
| 2019/0159782 A1 | 5/2019 | Kamaraj et al. |
| 2019/0167197 A1 | 6/2019 | Abunassar et al. |
| 2019/0183644 A1 | 6/2019 | Hacohen |
| 2019/0192296 A1 | 6/2019 | Schwartz et al. |
| 2019/0209323 A1 | 7/2019 | Metchik et al. |
| 2019/0261995 A1 | 8/2019 | Goldfarb et al. |
| 2019/0261996 A1 | 8/2019 | Goldfarb et al. |
| 2019/0261997 A1 | 8/2019 | Goldfarb et al. |
| 2019/0314155 A1 | 10/2019 | Franklin et al. |
| 2019/0321166 A1 | 10/2019 | Freschauf et al. |
| 2020/0113683 A1 | 4/2020 | Dale et al. |
| 2020/0138569 A1 | 5/2020 | Basude et al. |
| 2020/0205979 A1 | 7/2020 | O'Carroll et al. |
| 2020/0237512 A1 | 7/2020 | McCann et al. |
| 2020/0337842 A1 | 10/2020 | Metchik et al. |
| 2020/0360054 A1 | 11/2020 | Walsh et al. |
| 2020/0360132 A1 | 11/2020 | Spence |
| 2020/0368016 A1 | 11/2020 | Pesce et al. |
| 2021/0022850 A1 | 1/2021 | Basude et al. |
| 2021/0059680 A1 | 3/2021 | Lin et al. |
| 2021/0169650 A1 | 6/2021 | Dai et al. |
| 2021/0186698 A1 | 6/2021 | Abunassar et al. |
| 2021/0251757 A1 | 8/2021 | Siegel et al. |
| 2021/0259835 A1 | 8/2021 | Tyler, II et al. |
| 2021/0267781 A1 | 9/2021 | Metchik et al. |
| 2021/0307900 A1 | 10/2021 | Hacohen |
| 2021/0330456 A1 | 10/2021 | Hacohen et al. |
| 2021/0338418 A1 | 11/2021 | Feld |
| 2021/0361416 A1 | 11/2021 | Stearns |
| 2021/0361422 A1 | 11/2021 | Gross et al. |
| 2021/0361428 A1 | 11/2021 | Dixon |
| 2021/0401434 A1 | 12/2021 | Tien et al. |
| 2022/0039943 A1 | 2/2022 | Phan |
| 2022/0039954 A1 | 2/2022 | Nia et al. |
| 2022/0071767 A1 | 3/2022 | Dixon et al. |
| 2022/0133327 A1 | 5/2022 | Zhang et al. |
| 2022/0142780 A1 | 5/2022 | Zhang et al. |
| 2022/0142781 A1 | 5/2022 | Zhang et al. |

(56) References Cited

U.S. PATENT DOCUMENTS

| | | |
|---|---|---|
| 2022/0226108 A1 | 7/2022 | Freschauf et al. |
| 2022/0233312 A1 | 7/2022 | Delgado et al. |
| 2022/0257196 A1 | 8/2022 | Massmann |
| 2022/0287841 A1 | 9/2022 | Freschauf et al. |
| 2022/0313433 A1 | 10/2022 | Ma et al. |
| 2023/0014540 A1 | 1/2023 | Metchik et al. |

FOREIGN PATENT DOCUMENTS

| | | |
|---|---|---|
| CN | 106491245 A | 3/2017 |
| CN | 107789017 A | 3/2018 |
| CN | 109953779 A | 7/2019 |
| CN | 110338857 A | 10/2019 |
| CN | 110495972 A | 11/2019 |
| CN | 110537946 A | 12/2019 |
| CN | 110664515 A | 1/2020 |
| CN | 209996540 U | 1/2020 |
| CN | 211243911 U | 8/2020 |
| CN | 211723546 U | 10/2020 |
| CN | 111870398 A | 11/2020 |
| CN | 111904660 A | 11/2020 |
| CN | 112120831 A | 12/2020 |
| CN | 112168427 A | 1/2021 |
| CN | 112190367 A | 1/2021 |
| CN | 212346813 U | 1/2021 |
| CN | 212415988 U | 1/2021 |
| CN | 212490263 U | 2/2021 |
| CN | 113476182 A | 10/2021 |
| CN | 113855328 A | 12/2021 |
| CN | 215019733 U | 12/2021 |
| EP | 0098100 A2 | 1/1984 |
| FR | 2146050 A5 | 2/1973 |
| FR | 9711600 | 3/1997 |
| WO | 2014064694 A2 | 5/2014 |
| WO | 2017015632 A1 | 1/2017 |
| WO | 2018013856 A1 | 1/2018 |
| WO | 2018050200 A1 | 3/2018 |
| WO | 2018050203 A1 | 3/2018 |
| WO | 2018195015 A1 | 10/2018 |
| WO | 2018195201 A1 | 10/2018 |
| WO | 2018195215 A2 | 10/2018 |
| WO | 2019139904 A1 | 7/2019 |
| WO | 2020106705 A1 | 5/2020 |
| WO | 2020106827 A1 | 5/2020 |
| WO | 2020112622 A1 | 6/2020 |
| WO | 2020167677 A1 | 8/2020 |
| WO | 2020168081 A1 | 8/2020 |
| WO | 2020172224 A1 | 8/2020 |
| WO | 2020176410 A1 | 9/2020 |
| WO | 2021196580 A1 | 10/2021 |
| WO | 2021227412 A1 | 11/2021 |
| WO | 2022006087 A2 | 1/2022 |
| WO | 2022036209 A1 | 2/2022 |
| WO | 2022051241 A1 | 3/2022 |
| WO | 2022052506 A1 | 3/2022 |
| WO | 2022068188 A1 | 4/2022 |
| WO | 2022101817 A2 | 5/2022 |
| WO | 2022140175 A1 | 6/2022 |
| WO | 2022153131 A1 | 7/2022 |
| WO | 2022155298 A2 | 7/2022 |
| WO | 2022157592 A1 | 7/2022 |
| WO | 2022212172 A1 | 10/2022 |
| WO | 2023003755 A1 | 1/2023 |
| WO | 2023004098 A1 | 1/2023 |
| WO | 2023278663 A2 | 1/2023 |
| WO | 2023288003 A1 | 1/2023 |

OTHER PUBLICATIONS

Al Zaibag et al., "Percutaneous Balloon Valvotomy in Tricuspid Stenosis", British Heart Journal, vol. 57, No. 1, Jan. 1987.

Al-Khaja et al., "Eleven Years' Experience with Carpentier-Edwards Biological Valves in Relation to Survival and Complications", European Journal of Cardio-thoracic Surgery 3: pp. 305-311, 1989.

Andersen, H.R. "History of Percutaneous Aortic Valve Prosthesis," Herz No. 34. pp. 343-346. 2009.

Benchimol et al., "Simultaneous Left Ventricular Echocardiography and Aortic Blood Velocity During Rapid Right Ventricular Pacing in Man", The American Journal of the Medical Sciences, vol. 273, No. 1, pp. 55-62, 1977.

Dake et al., "Transluminal Placement of Endovascular Stent-Grafts for the Treatment of Descending Thoracic Aortic Aneurysms", The New England Journal of Medicine, vol. 331, No. 26, pp. 1729-1734, Dec. 29, 1994.

Dotter et al., "Transluminal Treatment of Arteriosclerotic Obstruction: Description of a New Technic and a Preliminary Report of Its Application", Circulation, vol. XXX, pp. 654-670, 1964.

Inoune, M.D., Kanji, et al., "Clinical Application of Transvenous Mitral Commissurotomy by a New Balloon Catheter," The Journal of Thoracic and Cardiovascular Surgery 87:394-402, 1984.

Lawrence, Jr., et al., "Percutaneous Endovascular Graft: Experimental Evaluation", Cardiovascular Radiology 163, pp. 357-360, May 1987.

Porstmann et al., "Der Verschluß des Ductus Arteriosus Persistens Ohne Thorakotomie", Thoraxchirurgie Vaskuläre Chirurgie, Band 15, Heft 2, Stuttgart, im Apr. 1967, pp. 199-203.

Rashkind et al., "Creation of an Atrial Septal Defect Without Thoracotomy: A Pallative Approach to Complete Transposition of the Great Arteries", The Journal of the American Medical Association, vol. 196, No. 11, pp. 173-174, Jun. 13, 1956.

Reul RM et al., "Mitral valve reconstruction for mitral insufficiency", Prog Cardiovasc Dis., vol. 39, Issue—6, May-Jun. 1997.

Rosch, M.D., Josef, "The Birth, Early Years and Future of Interventional Radiology," J Vasc Interv Radiol 2003; 14:841-853.

Sabbah et al., "Mechanical Factors in the Degeneration of Porcine Bioprosthetic Valves: An Overview", Journal of Cardiac Surgery, vol. 4, No. 4, pp. 302-309, Dec. 1989.

Selby et al., "Experience with New Retrieval Forceps for Foreign Body Removal in the Vascular, Urinary, and Biliary Systems", Radiology: 176. pp. 535-538, 1990.

Serruys et al., "Stenting of Coronary Arteries. Are we the Sorcerer's Apprentice?", European Heart Journal, 10, 774-782, pp. 37-45, 1989.

Sigwart, Ulrich, "An Overview of Intravascular Stents: Old and New," Chapter 48, Textbook of Interventional Cardiology, 2nd Edition, W.B. Saunders Company, Philadelphia, PA, © 1994, 1990, pp. 803-815.

Uchida et al., "Modifications of Gianturco Expandable Wire Stents", Technical Note, American Roentgen Ray Society, pp. 1185-1187, May 1988.

Watt et al., "Intravenous Adenosine in the Treatment of Supraventricular Tachycardia: A Dose-Ranging Study and Interaction with Dipyridamole", Br. J. Clin. Pharmac. 21, pp. 227-230, 1986.

Almagor et al., "Balloon Expandable Stent Implantation in Stenotic Right Heart Valved Conduits", Journal of the American College of Cardiology, vol. 16, No. 5, pp. 1310-1314, Nov. 15, 1990.

Batista RJ et al., "Partial left ventriculectomy to treat end-stage heart disease", Ann Thorac Surg., vol. 64, Issue—3, pp. 634-638, Sep. 1997.

Beall AC Jr. et al., "Clinical experience with a dacron velour-covered teflon-disc mitral-valve prosthesis", Ann Thorac Surg., vol. 5, Issue 5, pp. 402-410, May 1968.

Fucci et al., "Improved results with mitral valve repair using new surgical techniques", Eur J Cardiothorac Surg. 1995;Issue 9, vol. 11, pp. 621-626.

Maisano F et al., 'The edge-to-edge technique: a simplified method to correct mitral insufficiency', Eur J Cardiothorac Surg., vol. 13, Issue—3, pp. 240-245, Mar. 1998.

Pavonik, M.D., Ph.D., Dusan, et al. "Development and Initial Experimental Evaluation of a Prosthetic Aortic Valve for Transcatheter Placement," Cardiovascular Radiology 1992; 183:151-154.

Rashkind et al., "Historical Aspects of Interventional Cardiology: Past, Present, and Future", Texas Heart Institute Journal, Interventional Cardiology, pp. 363-367.

(56) References Cited

OTHER PUBLICATIONS

Ross, D.N, "Aortic Valve Surgery", Surgery of the Aortic Valves, Guy's Hospital, London, pp. 192-197.

Umaña JP et al., Bow-tie'mitral valve repair: an adjuvant technique for ischemic mitral regurgitation', Ann Thorac Surg., vol. 66, Issue—6, pp. 1640-1646, Nov. 1998.

Urban, Philip MD, "Coronary Artery Stenting", Editions Medecine et Hygiene, Geneve, pp. 1-47, 1991.

Wheatley, David J., "Valve Prosthesis", Rob & Smith's Operative Surgery, pp. 415-424, 1986.

Praz et al., "Compassionate use of the PASCAL transcatheter mitral valve repair system for patients with severe mitral regurgitation: a multicentre, prospective, observational, first-in-man study," Lancet vol. 390, pp. 773-780, 2017.

Andersen, et al., "Transluminal implantation of artificial heart valves. Description of a new expandable aortic valve and initial results with implantation by catheter technique in closed chest pigs." European Heart Journal (1992), 13, 704-708.

Kolata, Gina "Device That Opens Clogged Arteries Gets a Failing Grade in a New Study", The New York Times, Jan. 3, 1991, pp. 1-2 [online], [retrieved on Jul. 29, 2009]. Retrieved from the Internet <URL:http://www.nytimes.com/1991/01/03/health/device-that-opens-clogged-arteries-gets-a-faili . . . .

\* cited by examiner

MULTI-DIRECTION STEERABLE HANDLES

CROSS-REFERENCE TO RELATED APPLICATIONS

This application is a continuation of U.S. patent application Ser. No. 15/453,735, filed on Mar. 8, 2017, which claims the benefit of U.S. Provisional Patent Application No. 62/311,031 filed Mar. 21, 2016, which is incorporated by reference herein it its entirety.

FIELD

The present disclosure concerns control handles for steering an attached catheter or other transluminal device.

BACKGROUND

Transvascular techniques have been developed for introducing and implanting prosthetic devices, such as heart valves, into a patient's body using a flexible transvascular catheter in a manner that is less invasive than open heart surgery. Typical catheter control systems only allow for limited flexing of the distal end of the catheter, such as in two orthogonal axes perpendicular to the longitudinal axis of the catheter. For example, a conventional catheter control handle may include a lever or dial coupled to a pull wire running along one side of the catheter, such that actuating the lever or dial causes the distal tip of the catheter to flex radially to one side of the longitudinal axis. To cause the distal tip to flex in other directions, it is typically required to actuate additional levers/dials that are coupled to other pull wires. Thus, plural actuation devices typically have to be actuated at the same time in careful combinations or sequences to generate a desired degree of radial flexion in a desired circumferential direction.

SUMMARY

Disclosed herein are catheter control handles that utilize a cam based mechanism to provide improved steerability of an attached catheter. Utilizing a cam based mechanism for determining the circumferential angle and radial magnitude of the catheter flexion, independently from each other, gives the user more direct and fine control of the flexion. Some disclosed embodiments use axially movable sliders as cam followers that ride along a sloped cam surface for controlling the tension in catheter pull wires, while other embodiments use a ball-and-socket mechanism as a cam follower, and still other embodiments use a gimbal mechanism as a cam follower. The disclosed control handles allow for independent control of both the magnitude of radial flexion of an attached catheter and the circumferential angle in which the radial flexion occurs, without rotation of the entire catheter inside the patient. A clutch mechanism can also be included to fix the circumferential flexion angle while continuing to allow adjustment of the radial flexion angle.

The handle can comprise a flex knob, rotation of which causes axial adjustment of the cam member. The flex knob can be fixed relative to a central shaft that extends axially through the cam member and can be rotationally engaged with the housing to allow rotation of the flex knob and central shaft relative to the housing and restrict axial motion of the flex knob and central shaft relative to the housing. The central shaft can be engaged with the cam member such that rotation of the flex knob relative to the housing causes axial motion of the cam member relative to the housing.

The housing can further comprise a position knob fixed relative to the cam member, wherein rotation of the position knob causes rotational adjustment of the cam member. The position knob and the flex knob can be positioned adjacent to a distal end of the handle or adjacent to a proximal end of the handle.

The cam member can comprise a contact surface at one axial end that interfaces with the follower(s), and the contact surface can have a slope that varies in axial position as a function of circumferential position around the longitudinal axis of the handle. The slope of the cam member contact surface can vary gradually in axial position moving circumferentially around the contact surface, such that the follower(s) move gradually distally or proximally as the cam member is rotated about the longitudinal axis of the handle.

In some embodiments, each pull wire is coupled to its own slider or follower that slides along a longitudinal groove in the handle in response to its contact location along a cam member that can be rotated and translated. Rotation of the cam member causes some of the sliders to move distally and some of the sliders to move proximally, causing a change in the direction of the flexion. Linear translation of the cam member causes all of the sliders to slide together either distally or proximally, causing a change in the degree of flexion.

In some embodiments, a ball and socket mechanism is included such that the socket acts as a follower and is coupled to the pull wires, wherein the socket articulates about the ball in response to contact with a cam member. Rotation and translation of the cam member similarly causes independent changes to the direction of the flexion and to the degree of the flexion.

In some embodiments, a gimbal mechanism can be included in the handle to act as a cam follower. The pull wires can be coupled to an inner plate in the gimbal mechanism, and the inner gimbal plate can be actuated in multi-dimensions relative to the housing by rotation and translation of a cam member that is in contact with the gimbal plate. In some embodiments, pulley systems can be included in the handle to provide mechanical advantage in applying tension to the pull wires. In some embodiments, rack and pinon mechanisms can be included in the handle to provide mechanical advantage in applying tension to the pull wires and couple the pull wires to the cam/gimbal mechanism, which can help avoid bending and damage to the pull wires.

The foregoing and other objects, features, and advantages of the disclosed technology will become more apparent from the following detailed description, which proceeds with reference to the accompanying figures.

BRIEF DESCRIPTION OF THE DRAWINGS

FIG. 21 shows the control handle of FIG. 1 coupled to a flexible catheter, illustrating the steerability of the catheter using the control handle.

DETAILED DESCRIPTION

Figure 1:
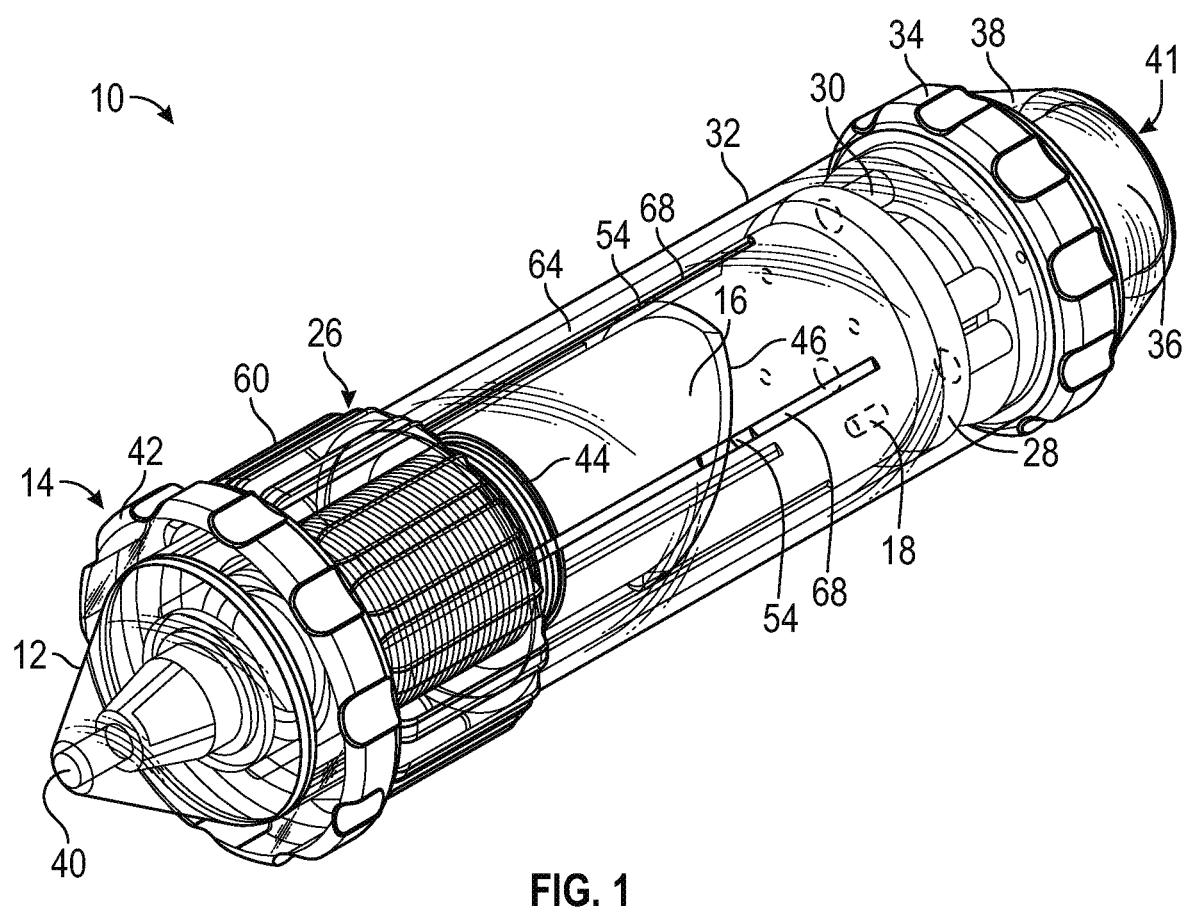
FIG. 1 is a perspective view of an exemplary cam-controlled multi-direction steerable control handle for performing a transvascular procedure, such as a delivery catheter for a prosthetic heart valve, which includes plural sliders that ride along a surface of a cam and control motion of a connected catheter.
Figure 2:
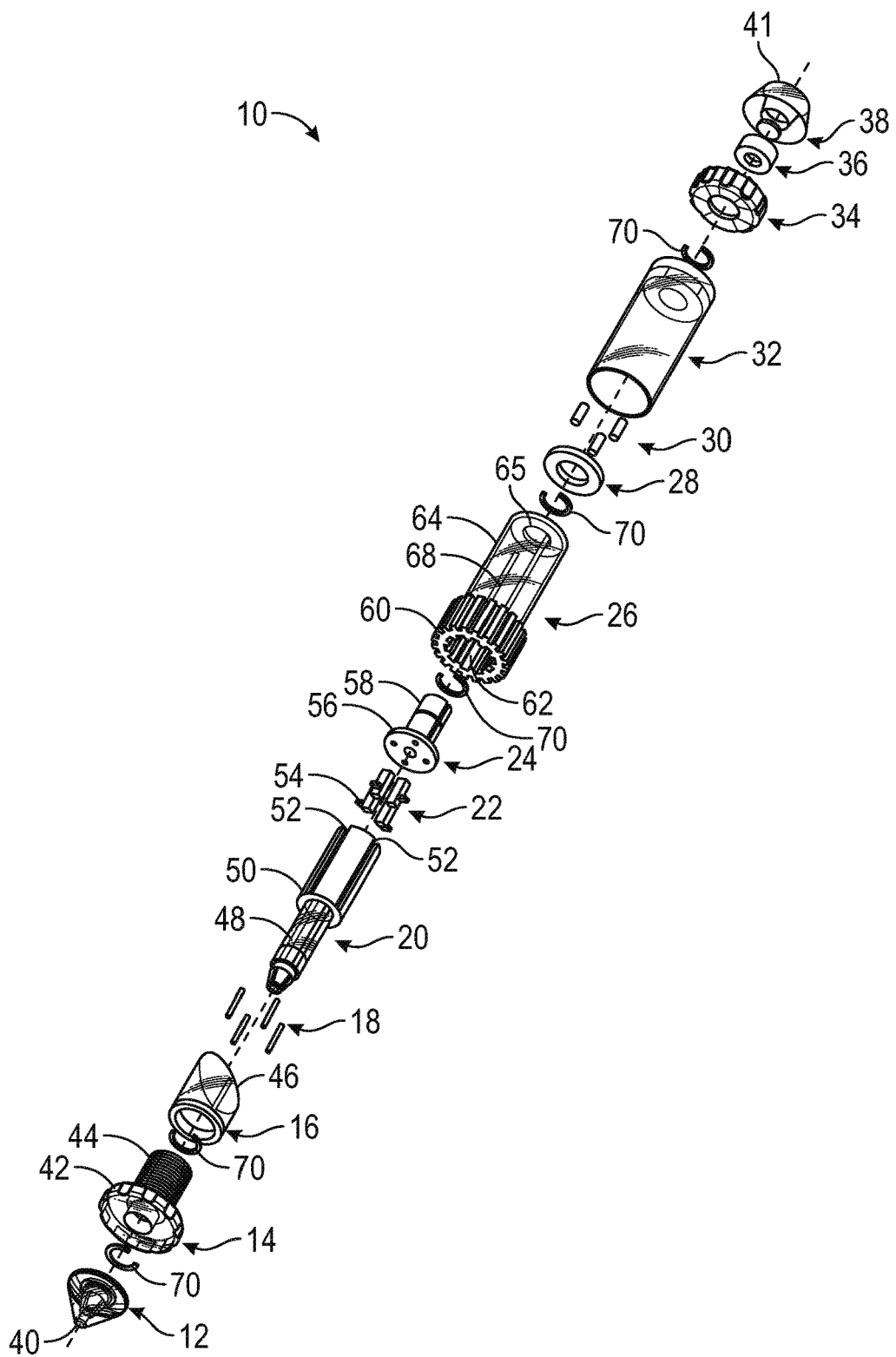
FIG. 2 is an exploded perspective view of the control handle of FIG. 1.

FIGS. 1 and 2 illustrate an exemplary catheter control handle 10 that provides cam-controlled multi-directional steerability for an attached catheter. A distal end 40 of the handle can be coupled to a transvascular catheter (see system 500 in FIG. 21) or other elongated and steerable tubular device for insertion into a patient, while a proximal end 41 may include luminal access for passage of other devices and/or fluids through the handle 10 and the attached catheter.

The handle 10 can comprise a cam member 16 having a sloped proximal surface 46 along which sliders 22 slide. The sliders 22 are constrained to only axial motion such that they act as cam followers. The sliders 22 can be coupled to pull wires running along sides of the catheter such that axial motion of the sliders 22 in slots 68 applies/changes tension on the associated pull wires. Any number of sliders and pull wires can be included.

The handle 10 can include a first knob 42 (referred to herein as the "flex knob") that causes axial translation of the cam 16, a second knob 60 (referred to herein as the "position knob") that causes circumferential rotation of the cam 16, and optionally a third knob 34 (referred to herein as the "clutch knob") that serves as a clutch or break to lock in the rotational position of the cam 16 selected by the second knob 60 while allowing adjustment to the axial position of the cam via the flex knob 42.

By rotating the flex knob 42, the user can cause the cam 16 to move axially relative to the rest of the handle, which causes all of the sliders 22 to move axially a corresponding distance, which in turn causes all of the pull wires attached to the sliders to increase or decrease in tension together, resulting in a change in the magnitude of the radial flexion of the distal tip of the attached catheter (but doesn't necessarily change to circumferential angle of the flexed catheter tip).

By rotating the position knob 60, the user can cause the cam 16 and its sloped end surface 46 to rotate around the central axis of the handle, causing one or more of the sliders 22 to move distally in the slots 68 and one or more other sliders to move proximally in the slots 68, depending on which part of the sloped end surface 46 is in contact with each slider 22. This can cause increased tension in one or more pull wires and simultaneous reduction in tension one or more other pull wires, which results in the flexed distal tip of the attached catheter pivoting about its central axis and changing the circumferential angle in which it is radially flexed (without rotating the whole catheter inside the patient.

Accordingly, each of the flex knob 42 and the position knob 60 can individually adjust all of the sliders 22 and associated pull wires with adjustment of a single knob, and each of the knobs 42 and 60 can generate a very different, yet complimentary, resultant adjustment to the distal tip of the catheter.

In one exemplary method, starting with the attached catheter having a straightened distal tip, the user can first rotate the flex knob 42 a sufficient amount to cause the distal tip of the catheter to flex radially to a desired angle from the longitudinal axis of the straightened position (e.g., to flexion angle of 30 degrees from straight). This flexion can be purely radial, with no circumferential motion (e.g., the radial flexion can occur while the distal tip is at a fixed circumferential angle of zero degrees). Then, the user can rotate the position knob 60 to cause the distal tip of the catheter to gradually change the circumferential angle in which it is radially flexed. For example, rotating the position knob 60 one direction can cause clockwise change in the circumferential angle of the distal tip, while rotating the position knob in the opposite direction can cause counter-clockwise change in the circumferential angle. This change in the circumferential angle can be caused while maintaining the degree of radial flexion of the distal tip. Furthermore, when the position knob 60 is used to change the circumferential angle of the distal tip flexion, the catheter itself does not need to be rotated inside the patient. Instead, the distal tip of the catheter is simply flexed in a different circumferential direction from straight while the rest of the catheter can remain stationary.

In another exemplary method, starting with the attached catheter having a straightened distal tip, the user can first rotate the position knob 60 to rotate the cam 16 to a selected circumferential position corresponding with the desired flexion direction of the distal tip of the catheter (e.g., 270 degrees clockwise from a designated reference point). Then, the user can rotate the flex knob 42 a sufficient amount to cause the distal tip of the catheter to flex radially in the desired direction to a desired angle from the longitudinal axis of the straightened position (e.g., to flexion angle of 30 degrees from straight). This flexion can be purely radial, with no circumferential motion (e.g., the radial flexion from zero to 30 degrees can occur while the distal tip is at the fixed circumferential angle of 270 degrees). Furthermore, after the desired circumferential angle is set with the position knob 60, the clutch knob 34 can be engaged to freeze the circumferential angle while permitting radial flexion of the distal tip using the flex knob 42.

As shown in FIGS. 1 and 2, the handle 10 includes a distal nose cone 12, a flex component 14 that can include the flex knob 41 and a threaded body 44, the cam 16, pins 18, a stationary slider guide 20 including distal body 48 and a proximal body 50 with slider grooves 52, the sliders 22 each having an outwardly projecting pin 54, a back plug 25 with a disk portion 56 and a proximal shaft 58, a positioning component 26 including the positioning knob 60 and a proximal cylinder 64 with slots/grooves 68, a washer 28, spacers 30, an outer sheath 32, the clutch knob 34, proximal gasket 36, and proximal end cap 38 forming the proximal end 41. Various retainers/fasteners (e.g., retaining rings 70)

can also be included. As shown in FIG. 1, the sliders 22 can slide axially along the grooves 52 while their slider pins 54 project out to the radial dimension of the cam 16. The cam 16 is positioned between the proximal body 50 and the proximal cylinder 64, such that the slider pins 54 contact the sloped proximal end surface 46 of the cam 16. The cam 16 can be coupled to the positioning component 26 such that rotation of the positioning knob 60 cause the cam to rotate, while at the same time the proximal cylinder 64 allows the cam to slide axially between the stationary slider guide 20 and the positioning component 26.

The threaded body 44 of the flex component 14 can be positioned around the distal body 48 of the stationary slider guide 20 and also engaged to the cam 16 such that rotation of the flex component 14 drives the cam axially relative to the stationary slider guide 20 and the cylinder 64 of the positioning component 26.

The clutch knob 34 can have an engaged position and a disengaged position. When in the engaged position, the position knob 60 can be locked such that the circumferential angle of distal tip is fixed, while allowing the flex knob 42 to drive the cam 16 axially and change the magnitude of radial flexion of distal tip. When the clutch knob 34 is in the disengaged position, both the flex knob and the position knob are functional.

Each of the sliders 22 can be attached to one end of a pull wire that runs distally through the handle 10, out the distal end 40, and along the attached catheter. The handle 10 can include 2, 3, 4, or more sliders and associated pull wires. Four sliders 22 are included in the illustrated embodiment, each spaced about 90 degrees apart from each other circumferentially.

The sloped proximal end surface 46 of the cam 16 can be configured to provide a desired balance between fine control of the flexion angles and a minimal amount of knob rotation that is necessary to adjust the flexion angles. For example, a steeper slope on the cam results is more change in radial flexion per degree of rotation of the flex knob, while a less sloped cam surface provide more fine control of the exact angle of flexion.

The sloped end surface 46 comprises a slider contact surface having a slope that varies in axial position as a function of circumferential position around the longitudinal axis of the handle. The slope of the contact surface can vary gradually in axial position moving circumferentially around the contact surface, such that the sliders move gradually proximally and distally as the cam is rotated about the longitudinal axis of the handle. The contact surface can comprise an annular surface that extends circumferentially around a central shaft and/or central lumen of the handle. The contact surface can comprise any planar or non-planar profile, such as a planar surface that defines an oblique plane that is not parallel or perpendicular to the longitudinal axis of the handle.

The flex knob 42 and the position knob 60 can be rotated at the same time or individually. For example, in an exemplary method, the two knobs can be rotated at the same time (in either the same rotational direction or in opposite rotational directions). Simultaneous rotation of the two knobs can cause the cam 16 to slide axially and rotate circumferentially at the same time, which causes the distal tip of the catheter to both change its degree of radial flexion and change the circumferential direction of the flexion.

The handle 10 can be manually operated with one hand or with two hands. Since the knobs 42 and 60 are close to each other, the user can operate both knobs with one hand while holding the handle 10.

The use of a cam feature in the disclosed control handles can provide an infinite degree of choice in selecting a desired flexion position of the distal tip of an attached catheter (see FIG. 21), as the cam feature can provide an analog adjustment mechanism. Furthermore, with regard to the control handle 10, an increased number of sliders and/or an increased number of different pull wires that are included and coupled to the sliders 22 can improve the smoothness of the analog control systems described herein.

Figure 21:
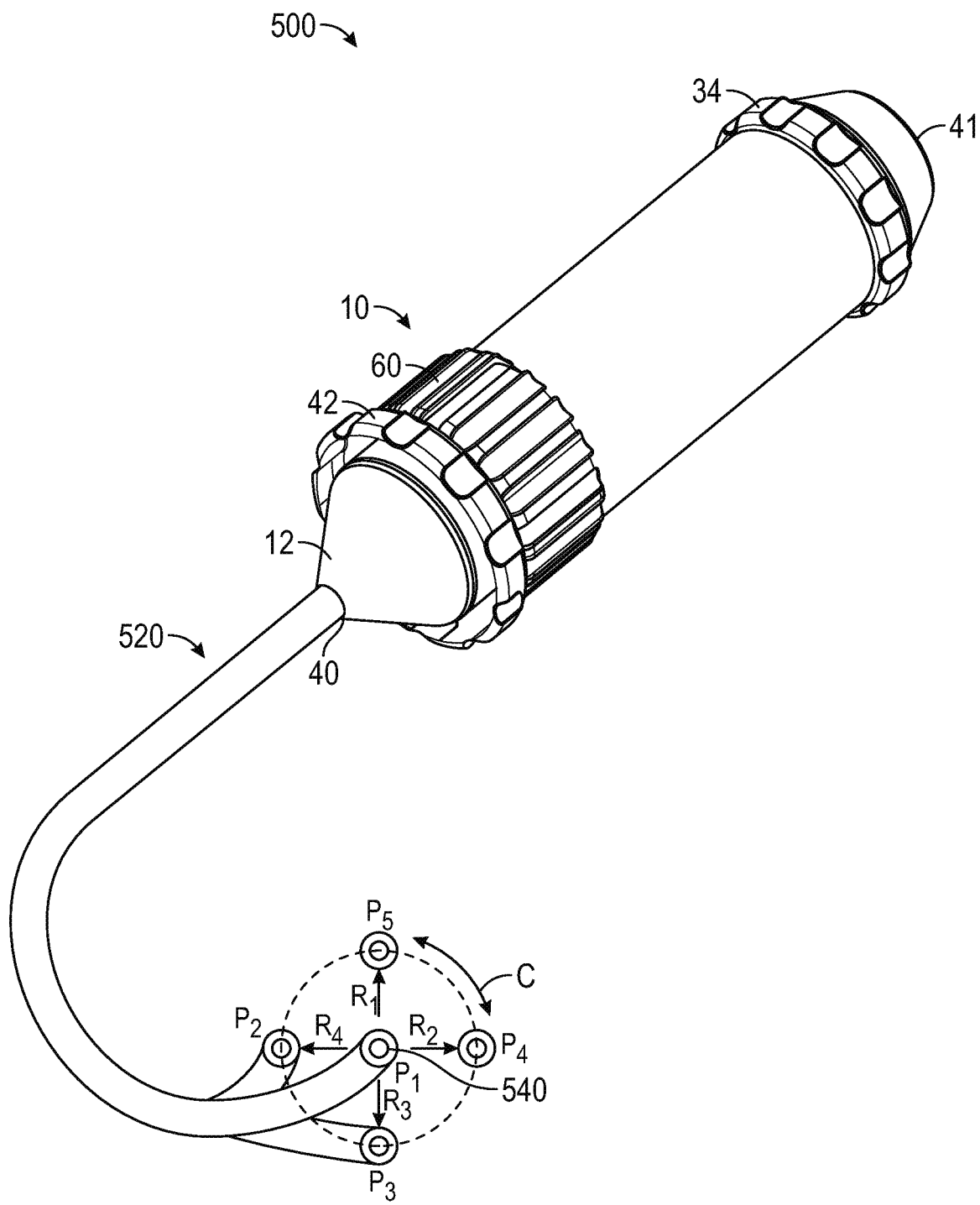
FIG. 21 shows the handles of FIG. 1 coupled to a catheter.

With reference to FIG. 21, rotating the flex knob 42 causes the catheter 520 to flex in a radial direction, such as any of the four exemplary radial direction R1, R2, R3, R4 labeled in FIG. 21, or direction in between the labeled directions. When the cam member 16 is in its distal position, the catheter can be relaxed and/or not flexed, such as is shown by the position P1 in FIG. 21. When the cam member is driven proximally, moving the slides proximally with it, the pull wires are tensioned, causing the catheter to flex radially, such as to any of the flexed positions labeled P1, P2, P3, P4 in FIG. 21. The circumferential angle in which the catheter flexes is determined by the position of the position knob 42. The rotational position of the position knob can correspond to circumferential motion of the flexed catheter in the directions labeled C. For example, if the catheter is currently in the flexed position P4, rotation of the position knob 60 degrees (while the flex knob is stationary) can move the catheter to position P3 or to position P5 along the dashed line (while the catheter does not rotate about its central longitudinal axis). If the catheter is currently in the unflexed position P1, rotation of the position knob may not cause any motion of the catheter (not even rotation of the catheter about its central longitudinal axis), but can determine in which radial direction (e.g., R1, R2, R3, R4) the catheter will flex when the flex knob is subsequently rotated. By adjusting the flex knob 42 and the position knob 60 in combination (simultaneously or one at a time), the catheter 520 can be steered to any flex position within the dashed circle in FIG. 21 (assuming the dashed circle represents the maximum degree of flexion), without rotating the catheter about its central longitudinal axis within a patient's body (rotation of the catheter within a vessel, for example, can damage the inner lining of the vessel).

Figure 3:
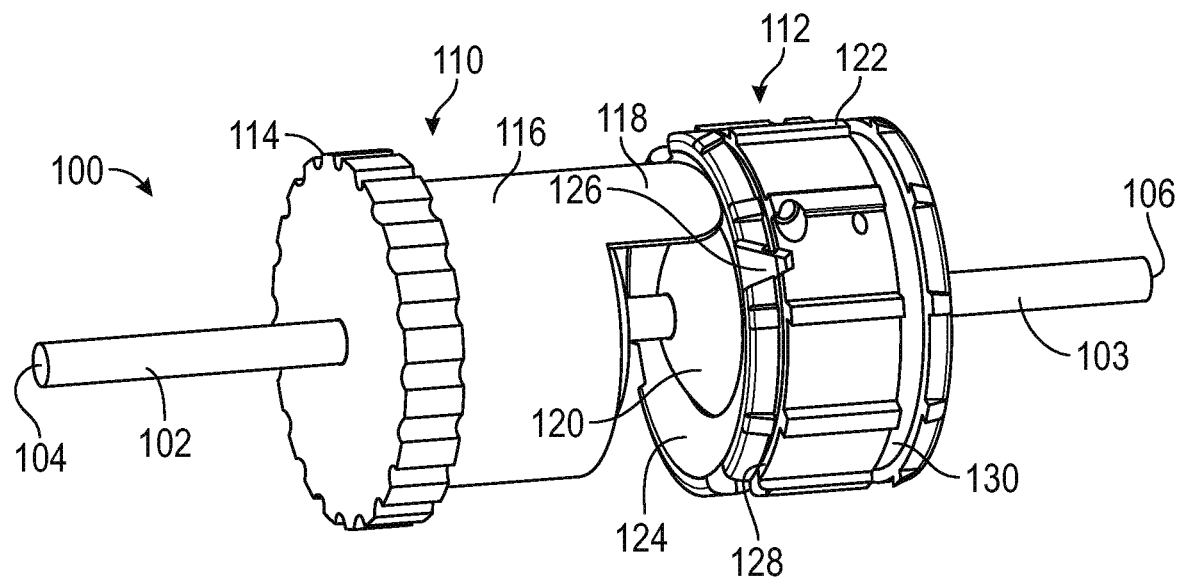
FIG. 3 is a perspective view of a portion of another cam-controlled steerable catheter control handle for a transvascular device, which includes a ball-and-socket cam mechanism.
Figure 4:
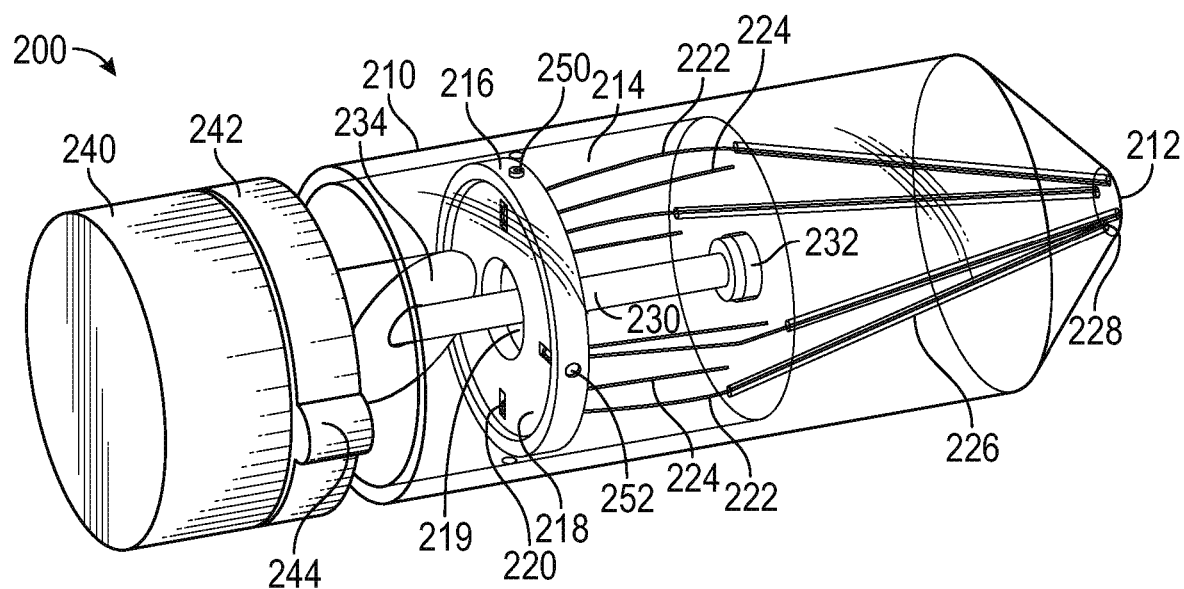
FIGS. 4-6 are perspective views of an exemplary cam-controlled multi-direction steerable catheter control handle including a gimbal mechanism.
Figure 5:
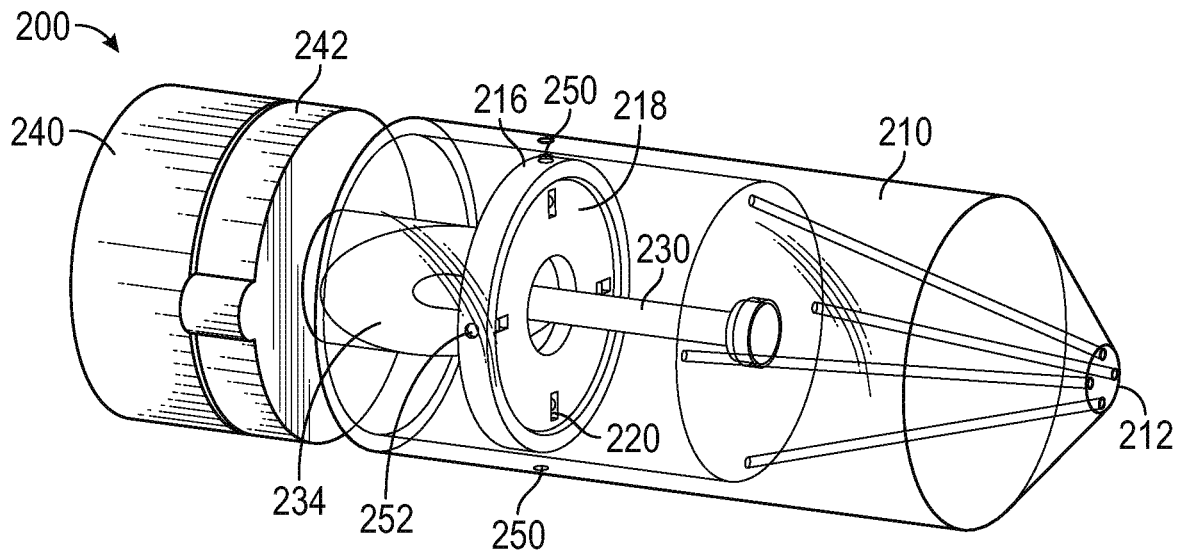
Figure 6:
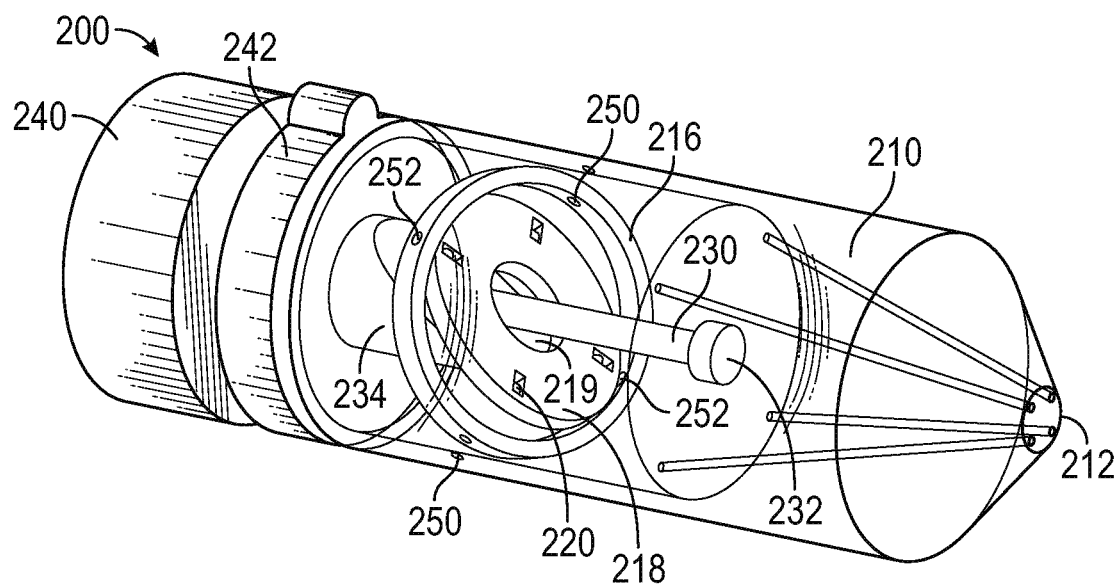

FIG. 3 illustrates another exemplary control handle 100 comprising a central tubular shaft 102, 103 having a distal end 104 and proximal end 106, a distal component 110 fixed to the shaft, a socket 112, and a ball 120 mounted on the shaft inside the socket. The distal component 110 includes a flex knob 114 and a cam body 116 with a proximally extending cam finger 118 that contacts a distal engagement surface 124 of the socket 112. The rotational orientation of the socket 112 relative to the cam finger 118 (e.g., selected be rotating the socket) determines which what the socket tilts relative to the ball 120, which determines the circumferential flexion angle of the distal tip of the catheter. The axial position of the cam finger 118 relative to the socket 112 (e.g., selected by rotation of the flex knob 114) determines the magnitude of axial flexion of the distal tip of the catheter. The socket 112 notches 126 and grooves 128, 130 around its outer perimeter. Plural guidewires are coupled to the socket around its perimeter and run distally into the catheter.

FIGS. 4-12 illustrate another exemplary control handle 200 that includes a cam member that interfaces with a gimbal mechanism to control tension on several different pull wires. The handle 200 comprises a housing 210 having a distal end 212 and a proximal inner cavity 214 that contains a gimbal mechanism comprising an outer gimbal ring 216 and an inner gimbal plate 218. The ring 216 is pivotably mounted relative to the housing 210 at pivot joints 250 so that the ring can rotate relative to the housing about a ring axis passing through joints 250 perpendicular to the longitudinal axis of the handle. The plate 218 is pivotably mounted relative to the ring 216 at pivot points 252 such that the plate can rotate relative to the ring about a plate axis passing through joints 252 perpendicular to the ring axis. The plate axis and ring axis are rotationally fixed about the housing axis, but the plate can pivot multidirectionally relative to the housing as the ring pivots relative to the housing through joints 250 and as the plate pivots relative to the ring through joints 252.

The gimbal plate 218 includes wire engagements 220 for each pull wire 222 of the handle. There maybe two, three, four, five, six, seven, eight, or more pull wires 222. Four pull wires 222 are illustrated as an example. Each wire 222 passes through passageways 226 in the handle and extends out from distal openings 228 into an attached catheter or other similar steerable device. FIG. 21 shows an exemplary catheter. The wires 222 can optionally loop around respective wire engagements 220 in the gimbal plate 218, as illustrated, such that end portions 224 of the wires extend back distally to fixed attachment points on the housing. In such embodiments, the wire engagements 220 can comprise a rounded peg, pulley, or other feature to facilitate the wires sliding around the wire engagement with minimal friction and kinking as the plate articulates. This arrangement can provide mechanical advantage, effectively halving the pulling force applied to the wires while causing the distal ends of the wires in the catheter to move at twice the rate that the wire engagements in the plate move. In alternative embodiments, the wires can terminate at the wire engagements 220 in the gimbal plate without any mechanical advantage, which can avoid bending the wires.

The handle 200 includes a central shaft 230 that has a distal end 232 coupled to the housing 210, an intermediate portion that passes through an opening 219 in the gimbal plate 218 and passing through cam member 234, and a proximal portion that is fixedly coupled to a proximal flex knob 240. The distal end 232 is coupled to the housing via a rotational bearing that allows rotation of the shaft 230 and knob 240 relative to the housing and gimbal mechanism, but prevents longitudinal motion of the shaft 230 and knob 240 relative to the housing and gimbal mechanism. Although not shown, the central shaft 230 and flex knob 240 can include a central lumen extending through their entire length. The housing 210 can also include a central lumen that extends from the distal end of the shaft 230 to the distal end 212 of the handle. Combined, the central lumens of the handle 200 can provide access for other devices and/or fluids to be passed into and out of a patient through the handle and through a connecting lumen in an attached catheter.

Figure 7:
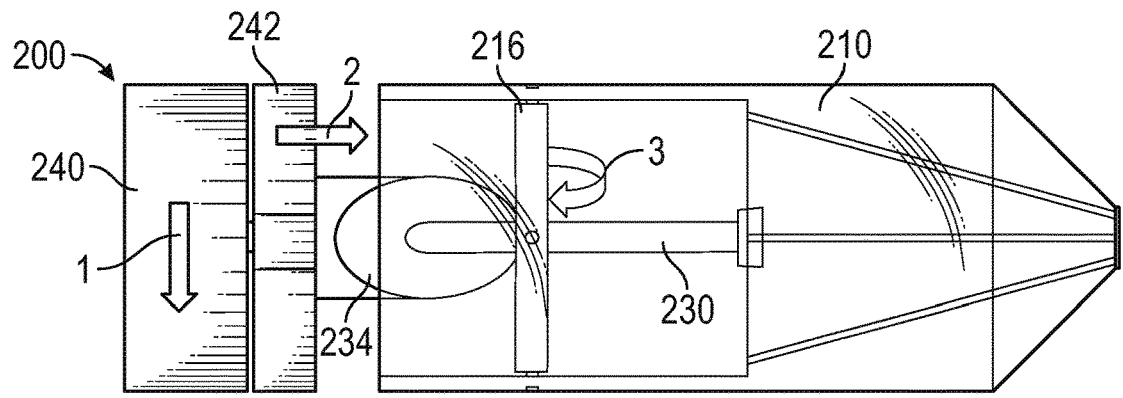
FIG. 7 is a side view of the handle of FIG. 4.
Figure 8:
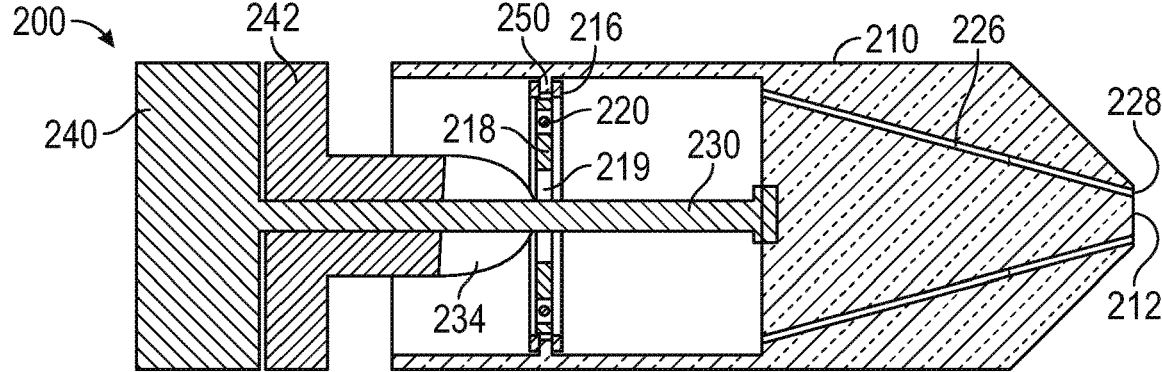
FIG. 8 is a side cross-section view of the handle of FIG. 4
Figure 9:
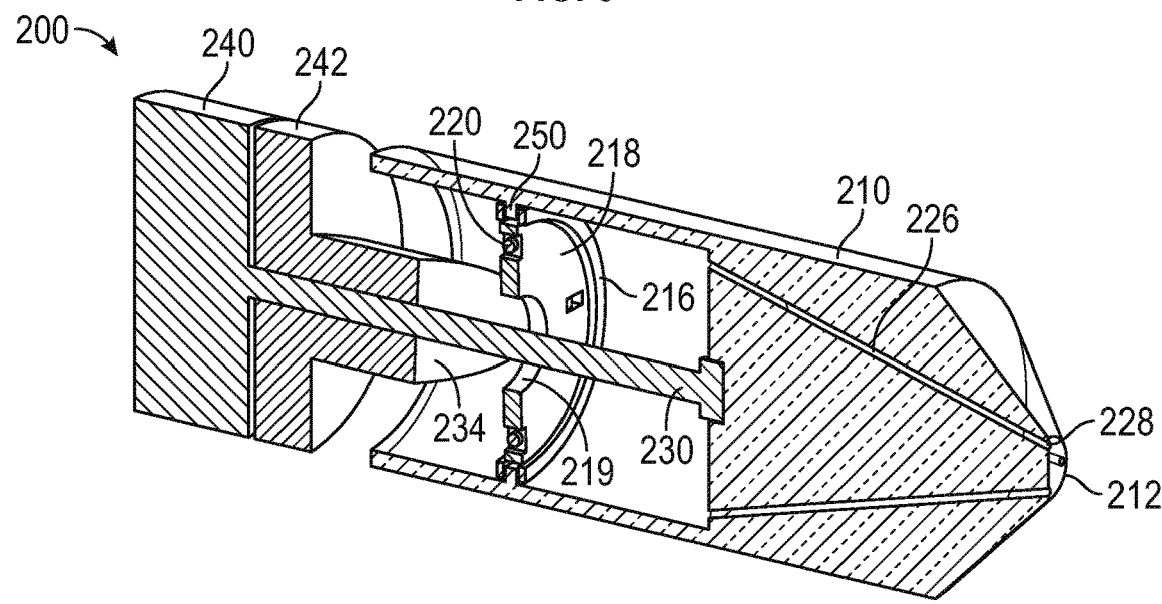
FIG. 9 is a perspective cross-section view of the handle of FIG. 4.

The handle 200 also includes a position knob 242 with indicator nub 242 that is fixedly coupled to the cam member 234 and positioned around the central shaft 230 distal to the flex knob 240. The cam member 234 and/or position knob 242 can be threadedly or helically engaged to the outer surface of the central shaft 230. As illustrated in FIG. 7, when the flex knob 240 and central shaft 230 are rotated (arrow 1) relative to the position knob 242 and cam member 234 (e.g., by holding the position knob stationary relative to the housing 210 and turning the flex knob), the position knob and cam member are driven distally (arrow 2) or proximally relative to the housing and gimbal mechanism, causing the gimbal plate to pivot (arrow 3) and change tension on all the pull wires.

By using the flex knob 240 to drive the cam member distally or proximally, the magnitude of the flexion of the catheter is adjusted. Distal motion of the cam causes the gimbal plate to tilt more, causing increased magnitude of flexion, and proximal motion of the cam member allows the gimbal plate to return closer to its natural position perpendicular to the longitudinal axis of the handle, reducing the flexion of the catheter. With reference to lower portion of FIG. 21, rotating the flex knob 240 causes the catheter to flex in the radial directions, such the four exemplary radial direction R1, R2, R3, R4 labeled in FIG. 21. When the cam member is in a proximal position, allowing the gimbal plate to be in its upright natural position, the catheter can be relaxed and/or not flexed, such as is shown by the position P1 in FIG. 21. When the cam member is driven distally, pivoting the gimbal plate, pull wires on one side are tensioned, causing the catheter to flex radially, such as to any of the flexed positions labeled P1, P2, P3, P4 in FIG. 21. The circumferential angle in which the catheter flexes is determined by the position of the position knob 244.

The sloped end surface of the cam member 234 comprises a gimbal plate contact surface having a slope that varies in axial position as a function of circumferential position around the longitudinal axis of the handle. The slope of the contact surface can vary gradually in axial position moving circumferentially around the contact surface, such that the gimbal plate 218 articulates gradually as the cam is rotated about the longitudinal axis of the handle. In some embodiments, only the end of the cam member 234 contacts the gimbal plate, and the same end part of the cam member remains in contact with the gimbal plate through the rotational range of motion of the cam member, making the exact shape of the sloped contact surface of the cam member less significant. However, in some embodiments, the contact surface can comprises an annular surface that extends circumferentially around the central shaft and/or a central lumen of the handle, and the contact surface can comprise any planar or non-planar profile, such as a planar surface that defines an oblique plane that is not parallel or perpendicular to the longitudinal axis of the handle.

In the illustrated example, the cam member 234 has a generally cylindrical radial outer surface and a sloped planar distal surface, forming an ovoid or elliptical distal surface that contacts the gimbal plate 218. In the illustrated example, the outer surface of the cam member is cylindrical and the distal surface of the cam member is planar, forming an elliptical perimeter of the distal surface, but in alternative embodiments the cam member can include non-cylindrical outer surfaces and/or non-planar distal surfaces, resulting in non-elliptical shapes of the distal surface. In addition, the radius of the cylindrical outer surface and/or the slope of the distal surface can be varied to adjust the profile of the distal surface. For example, a steeper or less steep slope at the distal end of the cam member can provide a greater or lesser magnitude of motion to the gimbal plate and thus greater or less range of motion to the pull wires.

Figure 10:
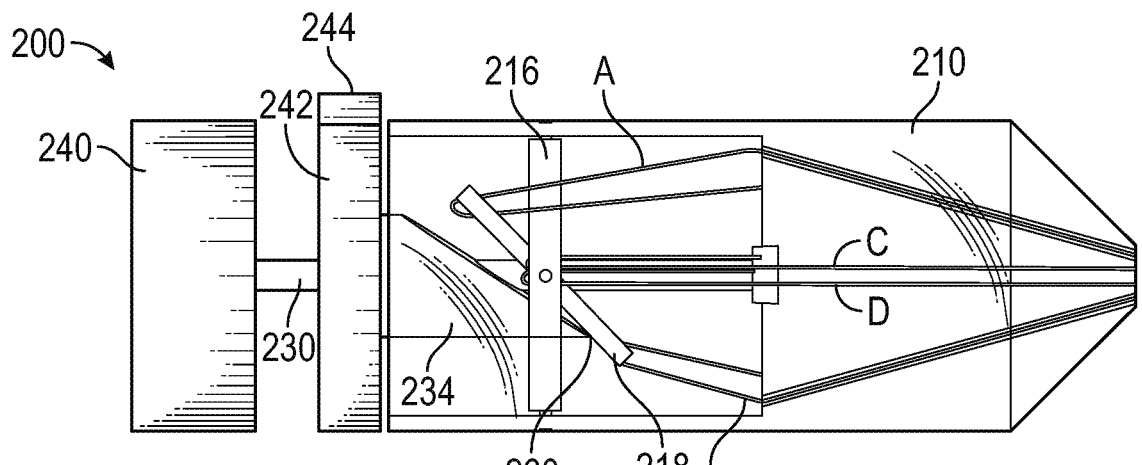
FIGS. 10-12 are side views showing various configurations of the handle of FIG. 4.
Figure 11:
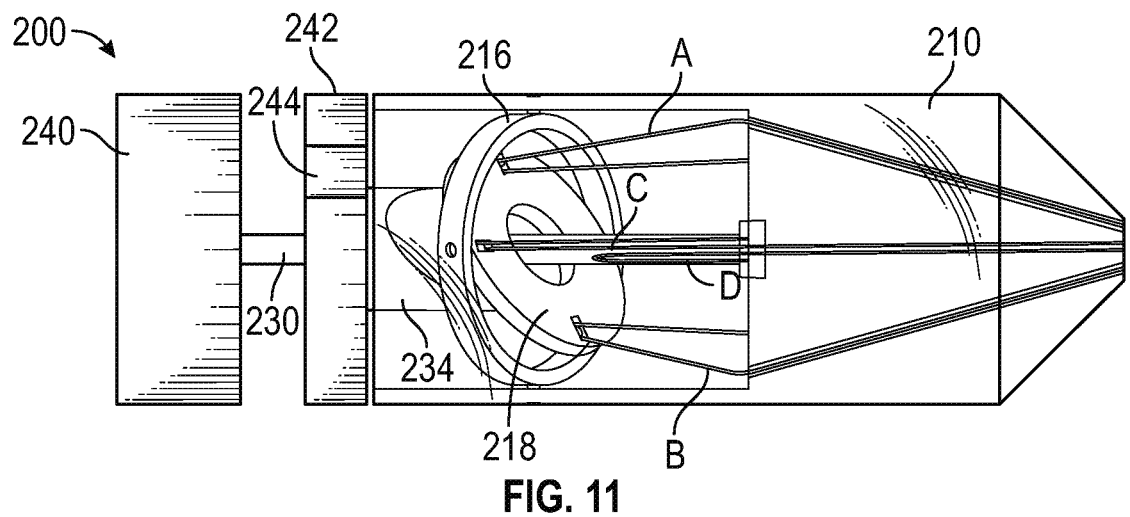
Figure 12:
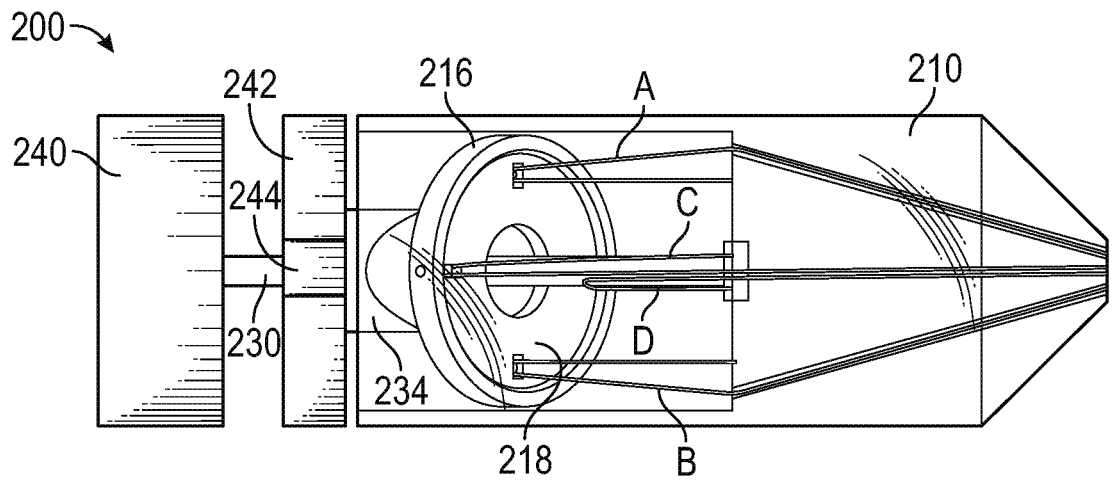
Figure 13:
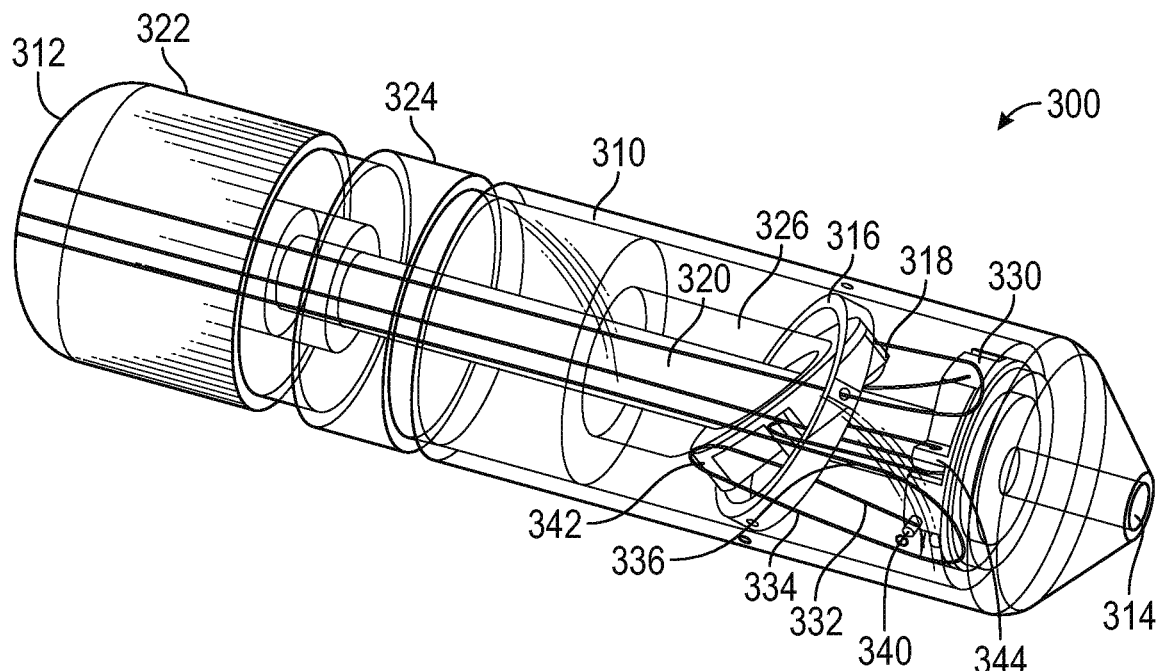
FIG. 13 is a perspective view of another exemplary cam-controlled multi-direction steerable handle including a gimbal mechanism.
Figure 14:
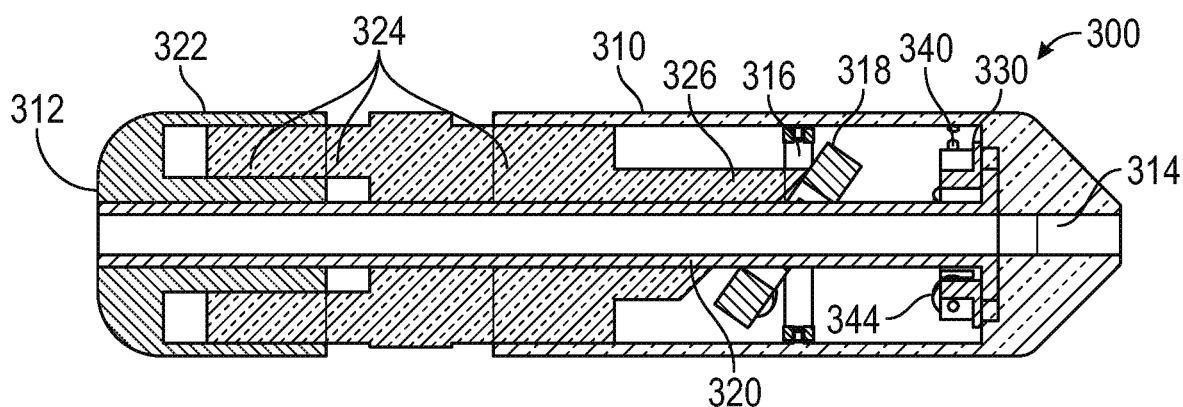
FIG. 14 is a side cross-section view of the handle of FIG. 13.

FIGS. 10-12 illustrate rotation of the position knob 242 to change the circumferential angle at which the catheter radially flexes. The rotational position of the position knob 242 can be visually and/or tactilely indicated by the nub 244 or other indicator. The position knob 242 and the attached cam member 234 can be rotated 360 degrees relative to the gimbal mechanism about the central shaft. The rotational position of the position knob determines where the distal edge of the cam member contacts the gimbal plate, and thus the direction in which the gimbal plate tilts when the flex knob is used to drive the cam member into the gimbal plate.

The gimbal ring 216 and gimbal plate 218 work together to allow the plate to tilt in any direction, and thus flex the catheter in any radial direction. In FIG. 10, the ring 216 is stationary and the plate 218 tilts about the plate axis, pulling on wire A and relaxing wire B. This causes the catheter to flex in the direction of the wire A. In FIG. 11, the ring 218 rotates about the ring axis and the plate 216 rotates about the plate axis, pulling both wires A and C, and relaxing wires B and D. This causes the catheter to flex in a direction between wires A and C. In FIG. 12, the plate 218 is stationary relative to the ring 216, and the ring and plate rotate in unison about the ring axis, pulling on wire C and relaxing wire D. This causes the catheter to flex in the direction of the wire C.

With reference to the lower portion of FIG. 21, the rotational position of the position knob can correspond to circumferential motion of the flexed catheter in the directions labeled C. For example, if the catheter is currently in the flexed position P4, rotation of the position knob 90 degrees (while the flex knob is stationary relative to the position knob) can move the catheter to position P3 or to position P5 along the dashed line (while the catheter does not rotate about its central longitudinal axis). If the catheter is currently in the unflexed position P1, rotation of the position knob may not cause any motion of the catheter (not even rotation of the catheter about its central longitudinal axis), but can determine in which radial direction (e.g., R1, R2, R3, R4) the catheter will flex when the flex knob is subsequently rotated.

By adjusting the flex knob and the position knob in combination (simultaneously or one at a time), the catheter can be steered to any flex position within the dashed circle in FIG. 21 (assuming the dashed circle represents the maximum degree of flexion), without rotating the catheter about its central longitudinal axis within a patient's body (rotation of the catheter within a vessel, for example, can damage the inner lining of the vessel).

In some embodiments, the gimbal plate can have a non-planar contact surface, with bump(s) and/or valley(s) which vary in height circumferentially and/or radially on the gimbal plate. These can compensate for any discretization effect of not using an infinite number of pull wires around the perimeter of the plate. For example, when the cam member pushes on the gimbal plate between two wires, it may need a little extra pull on the pull wires in order to get the same amount of flex at the distal end of the catheter. These bumps or valleys can achieve that extra pull by tilting the plate a little more or less at certain circumferential and radial cam contact locations. For example, if a completely planar gimbal plate is used, a slight unflexing may occur when the position knob is such that the flex direction is between two of the pull wires. Including a gradual bump on the gimbal plate in the location between the pull wire engagements (as just one example) can compensate for that expected unflexing by tilting the gimbal plate a little more when the cam contacts that bump, thereby providing the additional pull wire motion needed to maintain a constant flexion magnitude in a direction between two pull wires.

FIGS. 13-19 illustrate another exemplary control handle 300 that includes a cam member that interfaces with a gimbal mechanism to control tension on several different pull wires. The control handle 300 functions in a similar manner to the control handle 200, with the major difference being the catheter is connected to the opposite longitudinal end of the handle and the pull wires double back and extend out from the opposite longitudinal end of the handle, flipping what is the distal direction and what is the proximal direction compared to the handle 200.

The handle 300 comprises a housing 310 forming a proximal end 314, and the handle has a distal end 312 at or near flex knob 322. The flex knob 322 is axially fixed relative to the central shaft 320, and a position knob 324 is positioned around and/or within the flex knob in a threaded engagement or helical interface such that rotation of the flex knob drives the position knob and affixed cam member 326 axially relative to the gimbal mechanism inside the housing. The gimbal mechanism includes a gimbal ring 316 pivotably mounted inside the housing about a ring axis and a gimbal plate 318 pivotably mounted inside the ring via pivots along a plate axis perpendicular to the ring axis, like with the handle 200. The handle 300 also includes a wire guide plate 330 mounted inside the housing 310 proximal to the gimbal mechanism.

Each pull wire in the handle 300 has a free end 340 fixed to the wire guide plate 330, a first portion extending from the free end 340 distally to the gimbal plate 318 and around pulleys or other guides 342 in the gimbal plate, a second portion that extends back proximally from the gimbal plate to secondary pulleys or guides 344 in the wire guide plate 330, then around the pulleys or guides 344 to third portions that extend distally through the central shaft 320 along the length of the handle and out through the distal end 312 of the handle into catheter coupled to the handle.

Figure 15:
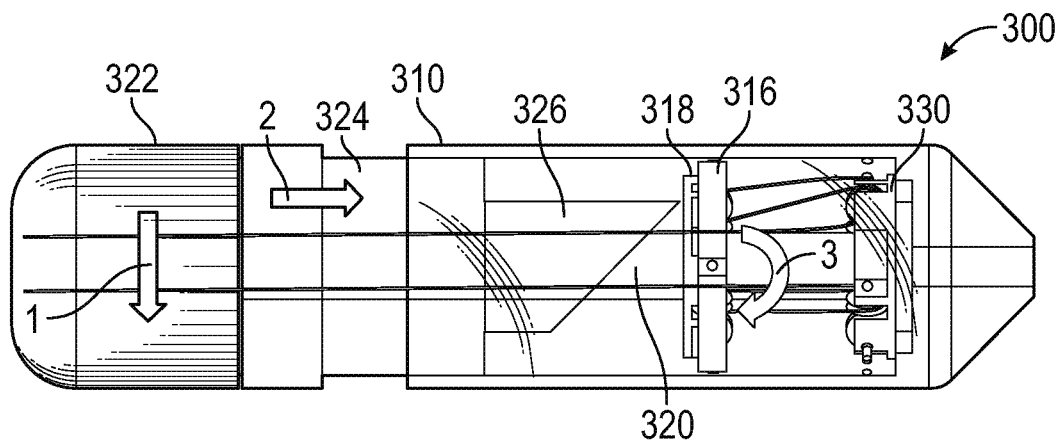
FIG. 15 is a side view of the handle of FIG. 13.

FIG. 15 illustrates how rotating the flex knob 322 (arrow 1) causes the cam member 326 to move axially (arrow 2), and cause the distal edge of the cam member to tilt the gimbal plate 318 and/or ring 316 (arrow 3), which adjusts the magnitude of flexion in the attached catheter.

Figure 16:
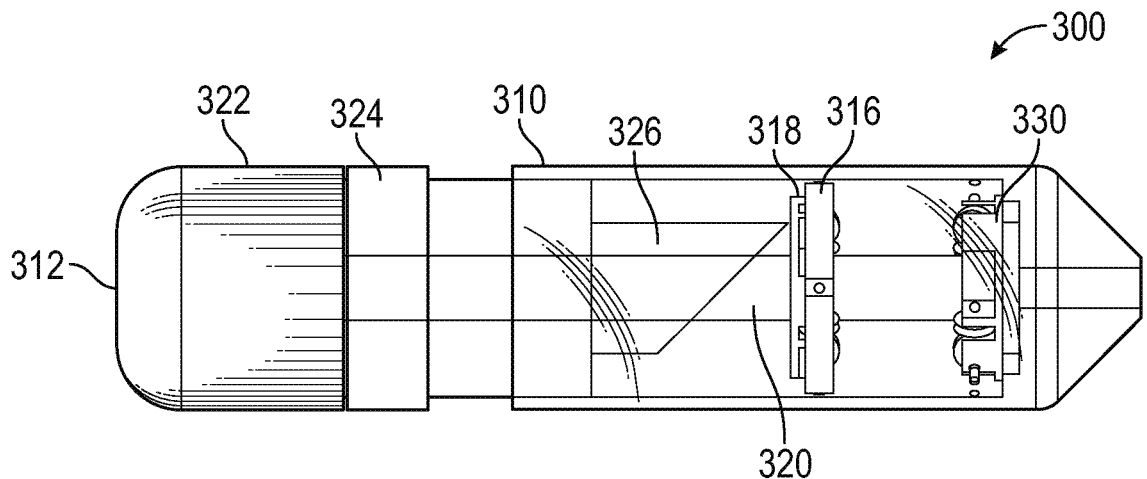
FIGS. 16-19 are side views showing various configurations of the handle of FIG. 13.
Figure 17:
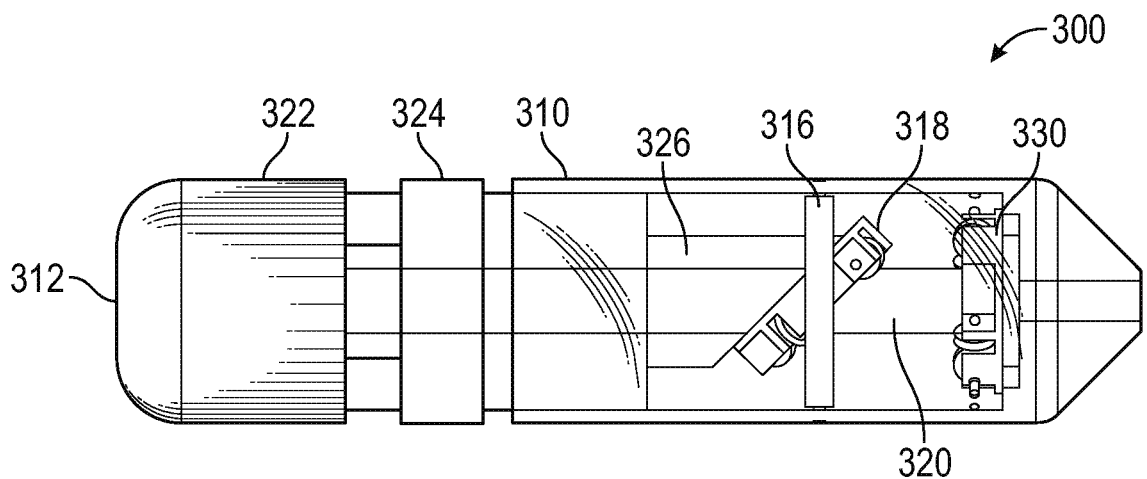
Figure 18:
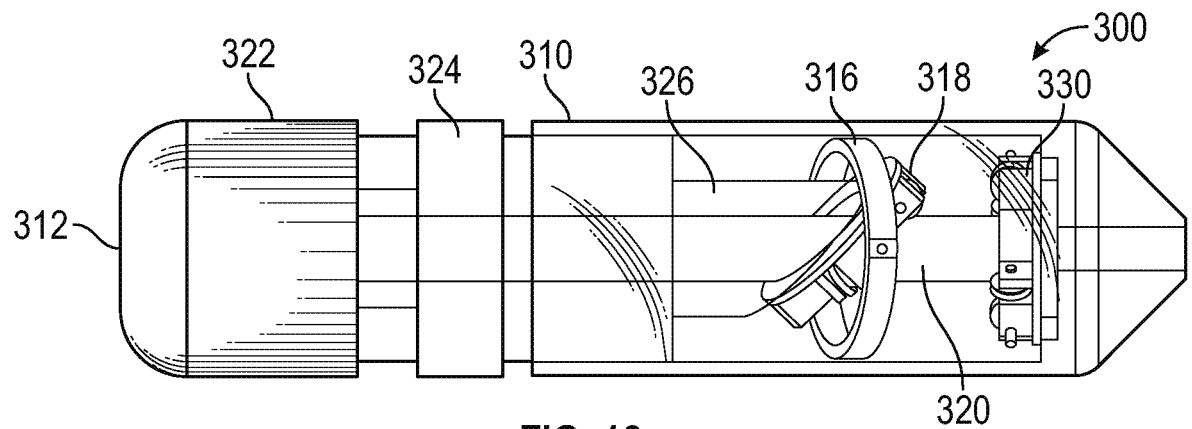
Figure 19:
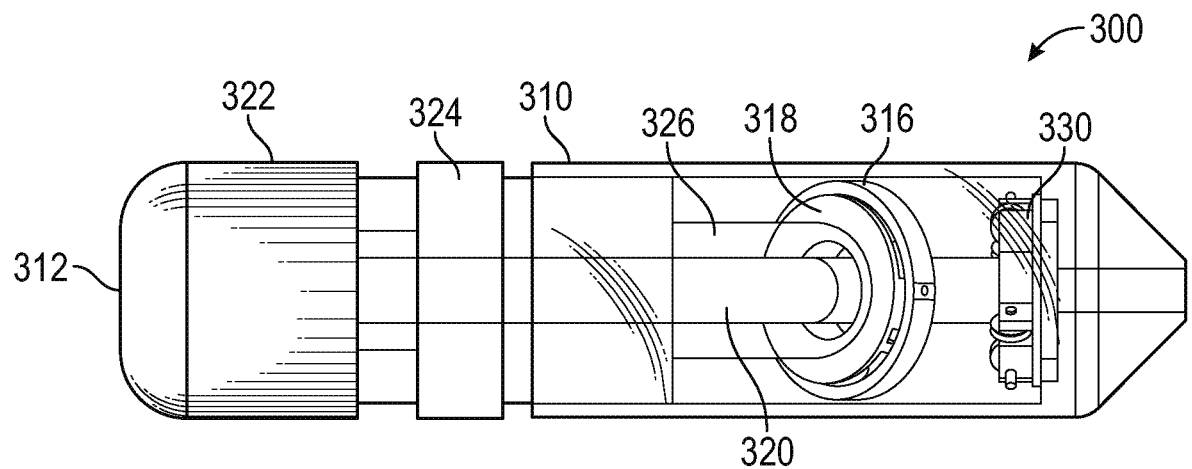

FIG. 16 shows the handle 300 with the gimbal ring 316 and plate 318 in the relaxed position when the cam member is not tilting them. In this state, the attached catheter can be in the relaxed, non-flexed neutral position. FIG. 17 shows the cam member 326 advanced proximally, tilting the gimbal plate 318 while the gimbal ring 316 remains stationary. This causes flexion of the attached catheter in a selected radial direction. FIG. 18 shows the cam member 326 has been rotated a few degrees from FIG. 17, such that both the gimbal plate and ring are pivoted. This causes the attached catheter to be flexed about the same magnitude but in a correspondingly different radial direction compared to FIG. 17. In FIG. 19, the cam member is rotated about 90 degrees from FIG. 17, such that the gimbal ring is pivoted relative to the housing 310, but the gimbal plate is not pivoted relative to the gimbal ring. In this position, the attached catheter is flexed about the same radial amount as in FIGS. 17 and 18, but it is flexed in a direction that is about 90 degrees from the direction corresponding the position of FIG. 17.

As the gimbal plate 318 moves relative to the wire guide plate 330, the pull wires articulate around the wire guides 342 and 344 in the two plates, providing a mechanical advantage that magnifies the relative small motions of the cam member and gimbal plate to provide the desired flexion in the catheter. Like with the handle 200, the mechanism system that couples the knobs 322 and 324 to the pull wires can be configured and/or calibrated to provide the desired balance of fine control and range of motion of catheter flexion. The gimbal mechanism also provides an analog, full 360 degree range of adjustability for the catheter flexion, without needing to rotate the catheter inside the patient.

Figure 20:
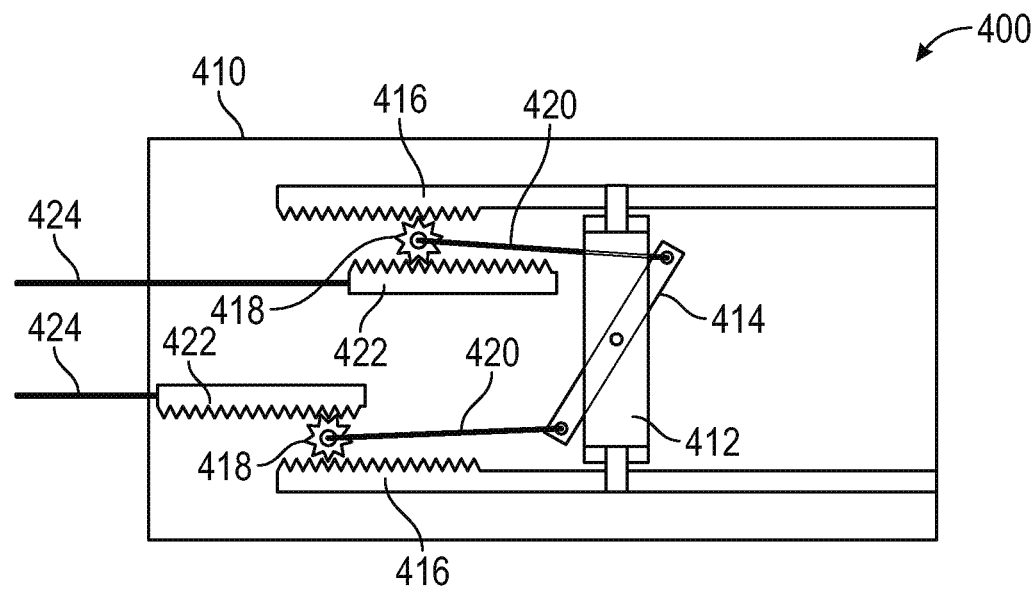
FIG. 20 is a schematic illustrating an alternative gimbal-based wire drive mechanism for a catheter control handle utilizing rack and pinion mechanisms for mechanical advantage in applying tension to the pull wires.

FIG. 20 is a schematic diagram that illustrates an alternative handle system 400 for coupling a gimbal mechanism to pull wires without looping or curling the pull wires. The system 400 includes a housing 410 with a gimbal ring 412 and gimbal plate 414 mounted inside the housing, fixed rack gears 416 mounted in fixed relationship to the housing, moving rack gears 422 opposing each fixed rack gear 416 and coupled to the pull wires 424, rolling pinon gears 418 engaged between the fixed and moving rack gears, and rigid connector members 420 coupled from the gimbal plate 414 to the center of each pinon gear 418. A cam member (not shown) causes motion of the gimbal mechanism, which pulls and pushes on the rigid connector members 420, causing the pinon gears 418 to roll correspondingly along the fixed rack gears 416. For each unit of distance the pinon gears 418 roll, the moving rack gears 422 move in the same direction but twice as far, creating mechanical advantage that magnifies the motion of the cam member into greater motion of the pull wires, but without pulleys or other devices that require the pull wires to be curled or bent around sharp angles, which can damage the wires over time.

It should be understood that the disclosed embodiments can be adapted to deliver and implant prosthetic devices in any of the native annuluses of the heart (e.g., the pulmonary, mitral, and tricuspid annuluses), and can be used with any of various approaches (e.g., retrograde, antegrade, transseptal, transventricular, transatrial, etc.). The disclosed embodiments can also be used to implant prostheses in other lumens of the body. Further, in addition to prosthetic valves, the delivery assembly embodiments described herein can be adapted to deliver and implant various other prosthetic devices such as stents and/or other prosthetic repair devices. In other embodiments, the disclosed devices can be used to perform various other transvascular surgical procedures other that implanting a prosthetic device.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the term "coupled" generally means physically, electrically, magnetically, and/or chemically coupled or linked and does not exclude the presence of intermediate elements between the coupled or associated items absent specific contrary language.

As used herein, the term "proximal" refers to a position, direction, or portion of a device that is closer to the user/operator of the device and further away from an end or destination of the device within a patient's body (e.g., the heart). As used herein, the term "distal" refers to a position, direction, or portion of a device that is further away from the user/operator of the device and closer to the end or destination of the device within a patient's body. Thus, for example, proximal motion of a catheter is motion of the catheter out of the body and/or toward the operator (e.g., retraction of the catheter out of the patient's body), while distal motion of the catheter is motion of the catheter away from the operator and further into the body (e.g., insertion of the catheter into the body toward the heart). The terms "longitudinal" and "axial" refer to an axis extending in the proximal and distal directions, unless otherwise expressly defined.

As used herein, the terms "integrally formed" and "unitary construction" refer to a one-piece construction that does not include any welds, fasteners, or other means for securing separately formed pieces of material to each other.

As used herein, operations that occur "simultaneously" or "concurrently" occur generally at the same time as one another, although delays in the occurrence of one operation relative to the other due to, for example, spacing, play or backlash between components in a mechanical linkage such as threads, gears, etc., are expressly within the scope of the above terms, absent specific contrary language.

In view of the many possible embodiments to which the principles of the disclosure may be applied, it should be recognized that the illustrated embodiments are only preferred examples and should not be taken as limiting the scope of the disclosure. Rather, the scope of the disclosed technology is at least as broad as the following claims. We therefore claim as our invention all that comes within the scope of these claims as well as their equivalents.

The invention claimed is:

1. A control handle for a steerable transluminal device, the control handle comprising:
   a housing defining a longitudinal axis extending in distal and proximal directions;
   pull wires that extend from a distal end of the housing and into the steerable transluminal device and that extend along an axial length of the steerable transluminal device and that are operable to effect flexion of the steerable transluminal device;
   a flex control member operable to control tension on the pull wires to adjust a magnitude of radial flexion of the steerable transluminal device;
   a position control member operable to control tension on the pull wires to adjust a circumferential angle in which the radial flexion of the steerable transluminal device is directed;
   a cam member that is movable axially relative to the housing and also movable rotationally about the longitudinal axis relative to the housing;
   at least one follower engaged with the cam member such that the at least one follower moves relative to the control handle in response to movement of the cam member relative to the housing;
   wherein the pull wires are coupled to the at least one follower;
   wherein rotation of the flex control member causes axial adjustment of the cam member; and wherein the position control member is fixed relative to the cam member and rotation of the position control member causes rotational adjustment of the cam member.

2. The control handle of claim 1, wherein the flex control member is operable to increase or decrease tension of all the pull wires to adjust the magnitude of radial flexion of the steerable transluminal device, and wherein the position control member is operable to increase tension in one or more pull wires and simultaneously reduce tension in one or more other pull wires to adjust the circumferential angle in which the radial flexion of the steerable transluminal device is directed.

3. The control handle of claim 1, further comprising a clutch mechanism having an engaged position operable to lock the position control member such that the circumferential angle of the steerable transluminal device is fixed while allowing operation of the flex control member to adjust the magnitude of radial flexion of the steerable transluminal device.

4. The control handle of claim 1, wherein the flex control member is fixed axially relative to a central shaft that extends axially through the cam member and is rotationally engaged with the housing to allow rotation of the flex control member relative to the housing and restrict axial motion of the flex control member and the central shaft relative to the housing.

5. The control handle of claim 1, wherein the cam member comprises a contact surface at one axial end that interfaces with the at least one follower, the contact surface having a slope that varies in axial position as a function of circumferential position around the longitudinal axis of the control handle, and wherein the slope of the cam member contact surface varies gradually in axial position moving circumferentially around the contact surface, such that the at least one follower moves gradually axially as the cam member is rotated about the longitudinal axis of the control handle.

6. The control handle of claim 1, wherein the at least one follower comprises a gimbal mechanism including a gimbal ring and a gimbal plate, wherein the gimbal ring is pivotably coupled within the housing and the gimbal plate is pivotably coupled within the gimbal ring.

7. The control handle of claim 1, wherein the flex control member and the position control member are independently operable to allow independent adjustment of the magnitude of radial flexion of the of the steerable transluminal device and independent adjustment of the circumferential angle in which the radial flexion of the steerable transluminal device is directed.

8. The control handle of claim 4, wherein the central shaft is engaged with the cam member such that rotation of the flex control member relative to the housing causes axial motion of the cam member relative to the housing.

9. The control handle of claim 5, wherein the cam member contact surface is a planar surface that defines an oblique plane that is not parallel or perpendicular to the longitudinal axis of the control handle.

10. The control handle of claim 6, wherein the pull wires are coupled to the gimbal plate, the cam member is in contact with the gimbal plate, and the position of the cam member determines an orientation of the gimbal mechanism, and the orientation of the gimbal mechanism determines axial positions of the pull wires.

11. The control handle of claim 6, wherein the pull wires are looped around wire guides in the gimbal mechanism, or the pull wires are looped around wire guides fixed relative to the housing proximal to the gimbal mechanism, or both.

12. The control handle of claim 10, wherein the gimbal plate comprises one or more bumps or valleys where the cam member contacts the gimbal plate, such that the cam member's axial position relative to the gimbal plate is slightly adjusted when the cam member contacts the one or more bumps or valleys.

13. The control handle of claim 7, wherein the magnitude of radial flexion of the steerable transluminal device and the circumferential angle in which the radial flexion of the steerable transluminal device is directed can be adjusted without rotating the steerable transluminal device about its longitudinal axis.

* * * * *